US008367747B2

(12) United States Patent
Bezwada

(10) Patent No.: US 8,367,747 B2
(45) Date of Patent: Feb. 5, 2013

(54) BIOABSORBABLE POLYMERS FROM BIOABSORBABLE POLYISOCYANATES AND USES THEREOF

(75) Inventor: Rao S. Bezwada, Hillsborough, NJ (US)

(73) Assignee: Bezwada Biomedical, LLC, Hills Borough, NJ (US)

( * ) Notice: Subject to any disclaimer, the term of this patent is extended or adjusted under 35 U.S.C. 154(b) by 669 days.

(21) Appl. No.: 12/470,977

(22) Filed: May 22, 2009

(65) Prior Publication Data

US 2009/0292029 A1 Nov. 26, 2009

Related U.S. Application Data

(60) Provisional application No. 61/055,546, filed on May 23, 2008.

(51) Int. Cl.
C08L 15/00 (2006.01)
A61K 6/00 (2006.01)
C08G 18/28 (2006.01)

(52) U.S. Cl. .......... 523/111; 523/118; 524/795; 528/52; 528/58; 560/8; 560/81; 560/82; 560/91; 560/103; 560/112; 560/129; 560/190; 560/330

(58) Field of Classification Search .................. 523/118
See application file for complete search history.

(56) References Cited

U.S. PATENT DOCUMENTS

| 4,826,945 | A |   | 5/1989 | Cohn |   |
|---|---|---|---|---|---|
| 4,829,099 | A | * | 5/1989 | Fuller et al. | 606/214 |
| 5,521,431 | A |   | 5/1996 | Tahara |   |
| 5,801,033 | A |   | 9/1998 | Hubbell |   |
| 5,834,274 | A |   | 11/1998 | Hubbell |   |
| 5,834,513 | A |   | 11/1998 | Ptchelintsev |   |
| 5,843,743 | A |   | 12/1998 | Hubbell |   |
| 5,932,229 | A |   | 8/1999 | Ptchelintsev |   |
| 6,221,997 | B1 |   | 4/2001 | Woodhouse |   |
| 6,887,974 | B2 |   | 5/2005 | Pathak |   |
| 8,048,980 | B2 |   | 11/2011 | Bezwada |   |
| 2003/0158598 | A1 |   | 8/2003 | Ashton |   |
| 2004/0096476 | A1 |   | 5/2004 | Uhrich |   |
| 2004/0170597 | A1 |   | 9/2004 | Beckman |   |
| 2005/0013793 | A1 |   | 1/2005 | Beckman |   |
| 2005/0238689 | A1 |   | 10/2005 | Carpenter |   |
| 2006/0013851 | A1 |   | 1/2006 | Giroux |   |
| 2006/0188547 | A1 | * | 8/2006 | Bezwada | 424/426 |
| 2007/0014755 | A1 |   | 1/2007 | Beckman |   |
| 2012/0197037 | A1 |   | 8/2012 | Bezwada |   |

FOREIGN PATENT DOCUMENTS

| EP | 295055 | 12/1988 |
| WO | WO 95/26762 | 10/1995 |
| WO | WO 2004/008101 | 1/2004 |
| WO | WO 2006/052790 | 5/2006 |
| WO | WO 2007/030464 | 3/2007 |

OTHER PUBLICATIONS van Dijk-Wolthuis, W.N.W.; Hoogeboom, J.; van Steenbergen, M.; Tsang, S.; and Hennick, W. "Degradation and Release Behavior of Dextran-Based Hydrogels", Macromolecules, 30; (1997) 4639-4645.
van Dijk-Wolthuis, W.N.E.; Tsang, S.; Kettenes-van den Bosch, J.; and Hennick, W. "A new class of polymerizable dextrans with hydrolysable groups: hydroxyethyl methacrylated dextran with and without oligolactate spacer", Polymer, 38 (25); (1997) 6235-6242.
Kurisawa et al, Macromol. Chem. Phys. 199, 705-709 (1998).
Heller, J.; Helwing, R.F.; Baker, R.W.; and Tuttle, M.E. "Controlled release of water-soluble macromolecules from bioerodible hydrogels" Biomaterials, 4; (1983) 262-266.
Brondsted (Brondsted, H.; and Kopccek, J. "Hydrogels for site-specific oral drug deliver: synthesis and characterization" Biomaterials, 12; (1991) 584-592.
Ulbrich, K.; Subr, V.; Seymour, L.W.; and Duncan, R. "Novel biodegradable hydrogels prepared using the divinylic crosslinking agent N, O-dimethacryloylhydroxylamine 1. Synthesis and characterization of rates of gel degradation, and rate of release of model drugs, in vitro and in vivo" Journal of Controlled Release, 24; (1993) 181-190.
Gutowska et al, J. Biomater. Res., 29, 811-21 (1995).
Hoffman, J. Controlled Release, 6, 297-305 (1987).
Mikos et al, Biomaterials, 14, 323-329 (1993).
Schugens et al, J. Biomed. Mater. Res., 30, 449-462 (1996).
Bulletin of the Material Research Society, Special Issue on Tissue Engineering (Guest Editor: Joachim Kohn), 21 (11), 22-26 (1996).
Remington's Pharmaceutical Sciences, 18$^{th}$ ed., Mack Publishing Company, Easton, PA, 1990 p. 1445.
Richard C. Larock, "Comprehensive Organic Transformations", VCH Publishers, New York, 1989, pp. 411-416.
Jerry Mar., "Advanced Organic Chemistry", 4$^{th}$ Ed., John Wiley and Sons, Inc., 1992, pp. 446, 660, 1216-1218, 1223, 1232-1233.

* cited by examiner

Primary Examiner — Richard Schnizer
Assistant Examiner — Laba Karki
(74) Attorney, Agent, or Firm — Vance Intellectual Property PC

(57) ABSTRACT

Novel bioabsorbable and/or biocompatible polyurethanes, polyureas, polyamideurethanes and polyureaurethanes with tunable physical, mechanical properties and hydrolytic degradation profiles are provided for use in biomedical applications such as stents, stent coatings, scaffolds, foams, and films. The disclosed polymers may be derived from biocompatible and/or bioabsorbable polyisocyanates. The present invention also relates to new and improved methods for the preparation of the biocompatible and/or bioabsorbable polyisocyanates.

36 Claims, No Drawings

BIOABSORBABLE POLYMERS FROM BIOABSORBABLE POLYISOCYANATES AND USES THEREOF

CROSS REFERENCE TO RELATED APPLICATION

This application claims the benefit of U.S. Provisional Application Ser. No. 61/055,546, filed May 23, 2008, the disclosure of which is hereby incorporated herein by reference in its entirety.

FIELD OF THE INVENTION

The present invention relates to bioabsorbable and/or biocompatible polyurethanes, polyureas, polyamideurethanes and/or polyureaurethanes with tunable physical, mechanical properties and/or hydrolytic degradation profiles and their uses. The disclosed polymers are useful, inter alia, in biomedical applications such as stents, stent coatings, tissue scaffolds, foams, and/or films wherein the bioabsorbable and biocompatible polyurethanes, polyureas, polyamideurethanes and/or polyureaurethanes are derived from bioabsorbable and/or biocompatible polyisocyanates. The present invention also relates to methods for the preparation of the bioabsorbable and/or biocompatible polyisocyanates.

BACKGROUND OF THE INVENTION

Absorbable polymers are increasingly used in a wide range of biomedical applications including tissue engineering scaffolds, stents, stent coatings, foams, and adhesion prevention barriers. This increased utilization is, in part, a function of the transient nature of these polymers when used as biomedical implants or drug carriers. Medical devices made from bioabsorbable polymers may have the potential to mitigate the inevitable and usually negative physiologic responses (e.g., fibrous encapsulation), which limit long-term device success. Hence, an array of bioabsorbable polymers have been developed and studied in various biomedical applications. While significant research and development activity has been carried out on bioabsorbable polymers, such polymers may suffer from performance deficiencies which are typically not fully recognized until new applications are identified and in-use testing has been carried out. As more uses for these materials are envisioned, an increased demand for bioabsorbable polymers with new and improved properties targeted to address performance deficiencies may be expected to follow.

The majority of bioabsorbable polymers are essentially hard and brittle. Relatively few of these bioabsorbable polymers are elastomeric. As interest in biomedical applications, such as tissue engineering scaffolds, stents, and/or stent coatings, and the like, has increased, bioabsorbable materials exhibiting a wider variety of additional physical properties have been identified to assist the integration of these polymers with the various tissues of the body.

Segmented polyurethane elastomers have enjoyed wide use as biomaterials generally due to their excellent mechanical properties and desirable chemical versatility. However, the vast majority of research devoted to the development of biomedical polyurethanes has focused on long-term applications such as vascular grafts and pacemaker lead insulators. In these types of applications, freedom from significant degradation is necessary to ensure stability of the long-term device. As a consequence, a significant amount of research designed to further inhibit the degradation of polyurethanes has been undertaken. This research indicates that the urethane, urea, and/or ester groups that may be present in a polyurethane or similar polymer have limited susceptibility to chemical and/or enzymatic hydrolysis in biological media. In addition, ether groups often present in the soft segment of a polyurethane or similar polymer may be susceptible to oxidative degradation via phagocyte-derived oxidants. This oxidative degradation is believed to be a key step in the stress cracking phenomenon found in pacemaker lead insulation.

Despite progress in the general development of polyurethanes and similar polymers for use in biomedical applications, relatively little research has been directed to developing bioabsorbable polyurethanes for temporary, rather than longer-term implantation. See Fuller et al., U.S. Pat. No. 4,829,099; Beckmann et al., U.S. Patent Publication Nos. 2005/0013793 A1, 2004/0170597 A1, and 2007/0014755 A1; Bruin et al., PCT Publication No. WO 95/26762; Woodhouse et al., U.S. Pat. No. 6,221,997; Cohn et al., U.S. Pat. No. 4,826,945, which generally discuss recent advances made in the field of bioabsorbable polyurethanes.

Subsequent work by Bruin et al., PCT Publication No. WO 95/26762 discloses the synthesis of crosslinked polyurethane networks incorporating lactide or glycolide and $\epsilon$-caprolactone joined by a lysine-based diisocyanate. Bruin discloses that these polymers display good elastomeric properties and degrade within about 26 weeks in vitro and about 12 weeks in vivo (subcutaneous implantation in guinea pigs). Despite their disclosed positive flexibility and degradation characteristics, these highly crosslinked polymers are not extensively used in some biomedical applications because they may not be readily processed into surgical articles, for example, using standard techniques such as solution casting or melt processing, as is the case for the more typical linear, segmented polyurethanes.

Cohn et al., EP 295055 discloses a series of elastomeric polyester-polyether-polyurethane block copolymers intended for use as surgical articles. However, these polymers may be relatively stiff and may have low tensile strength, which may preclude their use as elastomeric biomaterials. Beckmann et al., U.S. Patent Publication No. 2005/0013793 A1 describes polyurethane-based biodegradable adhesives from multi-isocyanate functional molecules and multifunctional precursor molecules with terminal groups selected from hydroxyl and amino groups. Woodhouse et al. discloses bioabsorbable polyurethanes derived from amino acids. However, all these bioabsorbable polyurethanes may suffer from one or more of the following drawbacks: (a) the very slow rate of formation of polyurethane that may be attributed to the low reactivity of the polyisocyanates, and (b) the lack of tunable physical and/or mechanical properties and/or controllable hydrolytic degradation profiles for biodegradable polyisocyanates or bioabsorbable polyurethanes derived therefrom.

Fuller et al. (U.S. Pat. No. 4,829,099) disclosed tissue adhesives based on biodegradable polyisocyanates. The synthetic methods used by Fuller et al. to prepare these biodegradable polyisocyanates may be quite cumbersome and/or cost ineffective.

Bezwada (U.S. Patent Application Publication No. 20060188547 A1 and WO 2007030464 A2) disclosed polyurethanes, the corresponding polyisocyanates, and preparations of their manufacture and use wherein the polyurethanes and/or polyisocyanates were reported to be bioabsorbable.

Shaped articles made from polyurethane polymers have been accepted for a variety of applications, including some biomedical applications. Generally speaking, the term "polyurethane" refers to a family of high strength, resilient synthetic polymeric materials containing recurring urethane, urea, and/or ester groups in the polymer backbone. While polyurethane polymers have certain useful properties, shaped articles based on these polymers are not typically bioabsorbable and may therefore be unacceptable in circumstances that require bioabsorption. For example, certain biomedical applications, such as surgical devices including but not limited to monofilament and multifilament sutures, films, sheets, plates, clips, staples, pins, screws, stents, stent coatings, and the like, generally require the use of a material that is bioabsorbable.

In addition, high strength, highly flexible, tough, and durable fibers that possess a prolonged flex fatigue life are needed for use as braided, knitted, woven, or non-woven implants to augment and/or temporarily reinforce autologous tissue grafts or to serve as scaffolds for tissue regeneration.

Other well known uses for bioabsorbable polymers that have not been fully realized or perfected with available polymers of the prior art include scaffolds for tissue engineering, bioabsorbable knitted vascular grafts, drug-releasing devices, growth factor-releasing implants for bone and tissue regeneration, and fiber-reinforced composites for orthopedic applications.

Despite advancements in the art of producing polymeric materials and methods for making polymeric materials suitable for use in stents, stent coatings, scaffolds, films, molded devices, and similar surgical articles, presently available polymers generally lack adequate performance properties desirable in surgical articles, for example, those related to bioabsorption, flex fatigue life, strength in use, flexibility and/or durability. Thus, there continues to be a need for new devices having tunable physical and/or biological properties, so that surgical articles having a variety of end uses can be prepared. The present invention is directed, inter alia, to absorbable stents, stent coatings, scaffolds, and/or flexible films with tunable physical and biological properties and other ends.

SUMMARY OF THE INVENTION

Accordingly, the present invention is directed, in part, to surgical articles or components thereof comprising a polyurethane, polyurea, polyamideurethane or polyureaurethane derived from a biocompatible and/or bioabsorbable polyisocyanate of Formula Ib:

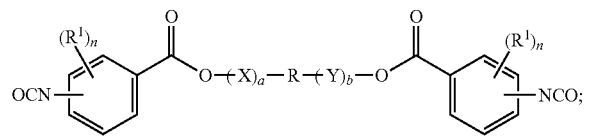

wherein:
R is alkylene-[C(R$^4$)(R$^5$)]$_s$-alkylene-, wherein:
   (1) one or more of the —CH$_2$— moieties in one or more alkylene chain portions of R are optionally replaced by —O— or —S—; or
   (2) one or more of the —CH$_2$—CH$_2$— moieties in the alkylene chain portions of R are optionally replaced by —C(=O)—O— or —O—C(=O)—;
each R$^1$ is independently [—C(R$^2$)(R$^3$)—]$_p$-Z;
each Z is independently alkoxy, aralkyloxy, —C(=O)—H, halogen, —C(=O)—OH, or —NO$_2$;
each R$^2$ and R$^3$ is independently H or alkyl;
R$^4$ is H, alkyl, (Y$^1$)$_c$OR$^6$, OR$^6$, CH$_2$—(Y$^2$)$_d$OR$^6$, or CH$_2$OR$^6$;

R$^5$ is H, alkyl, CH$_2$—(Y$^2$)$_d$OR$^6$, or CH$_2$OR$^6$;
each R$^6$ is independently:

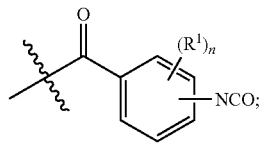

each X is independently —CH(CH$_3$)—C(=O)—O—, —(CH$_2$)$_y$—C(=O)—O—, or —(CH$_2$CH$_2$O)$_z$—CH$_2$—C(=O)—O—;
each Y, Y$^1$, and Y$^2$ is independently —O—C(=O)—CH(CH$_3$)—, —O—C(=O)—(CH$_2$)$_y$, or —O—C(=O)—CH$_2$—(OCH$_2$CH$_2$)$_z$—;
each a, b, c, and d is independently an integer from about 1 to about 6;
n is an integer from about 0 to about 4;
p is an integer from about 0 to about 10;
s is the integer 0 or 1; and
each y and z is independently an integer from about 1 to about 24.

In other embodiments, the invention is directed to pharmaceutical compositions comprising a polymeric carrier and a drug uniformly dispersed therein;
wherein the polymeric carrier comprises a polyurethane, polyurea, polyamideurethane and/or polyureaurethane derived from a biocompatible and bioabsorbable polyisocyanate of Formula Ib:

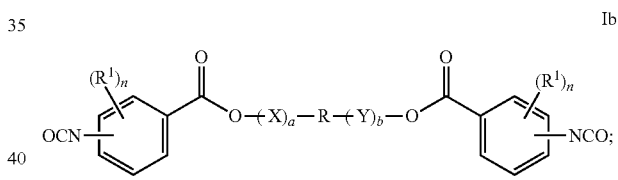

wherein:
R is alkylene-[C(R$^4$)(R$^5$)]$_s$-alkylene-, wherein:
   (1) one or more of the —CH$_2$— moieties in one or more alkylene chain portions of R are optionally replaced by —O— or —S—; or
   (2) one or more of the —CH$_2$—CH$_2$— moieties in the alkylene chain portions of R are optionally replaced by —C(=O)—O— or —O—C(=O)—;
each R$^1$ is independently [—C(R$^2$)(R$^3$)—]$_p$-Z;
each Z is independently alkoxy, aralkyloxy, —C(=O)—H, halogen, —C(=O)—OH, or —NO$_2$;
each R$^2$ and R$^3$ is independently H or alkyl;
R$^4$ is H, alkyl, (Y$^1$)$_c$OR$^6$, OR$^6$, CH$_2$—(Y$^2$)$_d$OR$^6$, or CH$_2$OR$^6$;
R$^1$ is H, alkyl, CH$_2$—(Y$^2$)$_d$OR$^6$, or CH$_2$OR$^6$;
each R$^6$ is independently:

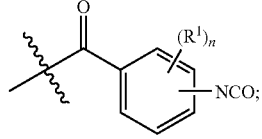

each X is independently —CH(CH₃)—C(=O)—O—, —(CH₂)ᵧ—C(=O)—O—, or —(CH₂CH₂O)_z—CH₂—C(=O)—O—;

each Y, Y¹, and Y² is independently —O—C(=O)—CH(CH₃)—, —O—C(=O)—(CH₂)ᵧ—, or —O—C(=O)—CH₂—(OCH₂CH₂)_z—;

each a, b, c, and d is independently an integer from about 1 to about 6;

n is an integer from about 0 to about 4;

p is an integer from about 0 to about 10;

s is the integer 0 or 1; and each y and z is independently an integer from about 1 to about 24.

In other embodiments, the present invention is directed to processes for preparing biocompatible and/or bioabsorbable polyisocyanate compounds of Formula Ib:

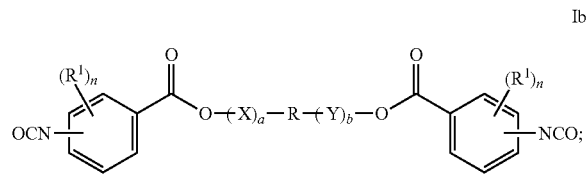

wherein:
R is alkylene-[C(R⁴)(R⁵)]_s-alkylene-, wherein:
(1) one or more of the —CH₂— moieties in one or more alkylene chain portions of R are optionally replaced by —O— or —S—; or
(2) one or more of the —CH₂—CH₂— moieties in the alkylene chain portions of R are optionally replaced by —C(=O)—O— or —O—C(=O)—;

each R¹ is independently [—C(R²)(R³)—]_p-Z;

each Z is independently alkoxy, aralkyloxy, —C(=O)—H, halogen, —C(=O)—OH, or —NO₂;

each R² and R³ is independently H or alkyl;

R⁴ is H, alkyl, (Y¹)_cOR⁶, OR⁶, CH₂—(Y²)_dOR⁶, or CH₂OR⁶;

R⁵ is H, alkyl, CH₂—(Y²)_dOR⁶, or CH₂OR⁶;

each R⁶ is independently:

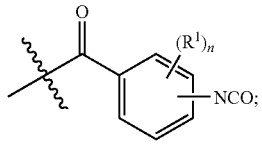

each X is independently —CH(CH₃)—C(=O)—O—, —(CH₂)ᵧ—C(=O)—O—, or —(CH₂CH₂O)_z—CH₂—C(=O)—O—;

each Y, Y¹, and Y² is independently —O—C(=O)—CH(CH₃)—, —O—C(=O)—(CH₂)ᵧ—, or —O—C(=O)—CH₂—(OCH₂CH₂)_z—;

each a, b, c, and d is independently an integer from about 1 to about 6;

n is an integer from about 0 to about 4;

p is an integer from about 0 to about 10;

s is the integer 0 or 1; and each y and z is independently an integer from about 1 to about 24;

comprising contacting a compound of Formula II:

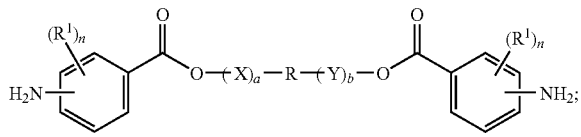

with triphosgene;

for a time and under conditions effective to provide the compound of Formula Ib.

The present invention is also directed, in part, to surgical articles or components thereof comprising a polyurethane, polyurea, polyamideurethane or polyureaurethane derived from a biocompatible and/or bioabsorbable polyisocyanate of Formula I:

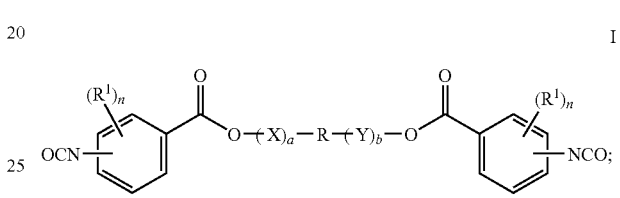

wherein:
R is alkylene-[C(R⁴)(R⁵)]_s-alkylene-, wherein:
(1) one or more of the —CH₂— moieties in one or more alkylene chain portions of R are optionally replaced by —O— or —S—; or
(2) one or more of the —CH₂—CH₂— moieties in the alkylene chain portions of R are optionally replaced by —C(=O)—O— or —O—C(=O)—;

each R¹ is independently [—C(R²)(R³)—]_p-Z;

each Z is independently alkoxy, aralkyloxy, —C(=O)—H, halogen, —C(=O)—OH, or —NO₂;

each R² and R³ is independently H or alkyl;

R⁴ is H, OR⁶ or CH₂OR⁶;

R⁵ is H or CH₂OR⁶;

R⁶ is

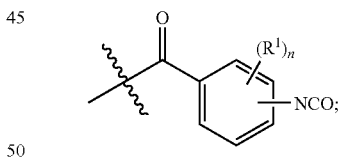

each X is independently —CH(CH₃)—C(=O)—O—; —(CH₂)ᵧ—C(=O)—O—; or —(CH₂CH₂O)_z—CH₂—C(=O)—O—;

each Y is independently —O—C(=O)—CH(CH₃)—, —O—C(=O)—(CH₂)ᵧ—, or —O—C(=O)—CH₂—(OCH₂CH₂)_z—;

each a and b is independently an integer from about 1 to about 6;

n is an integer from about 0 to about 4;

p is an integer from about 0 to about 10;

s is the integer 0 or 1; and each y and z is independently an integer from about 1 to about 24.

In other embodiments, the invention is directed to pharmaceutical compositions comprising a polymeric carrier and a drug uniformly dispersed therein;

wherein the polymeric carrier comprises a polyurethane, polyurea, polyamideurethane and/or polyureaurethane derived from a biocompatible and bioabsorbable polyisocyanate of Formula I:

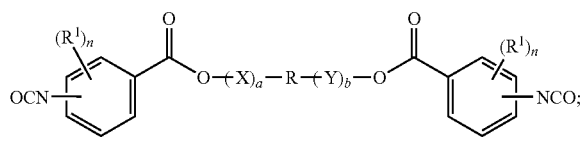

wherein:

R is alkylene-[C(R$^4$)(R$^5$)]$_s$-alkylene-, wherein:
   (1) one or more of the —CH$_2$— moieties in one or more alkylene chain portions of R are optionally replaced by —O— or —S—; or
   (2) one or more of the —CH$_2$—CH$_2$— moieties in the alkylene chain portions of R are optionally replaced by —C(=O)—O— or —O—C(=O)—;

each R$^1$ is independently [—C(R$^2$)(R$^3$)—]$_p$-Z;
each Z is independently alkoxy, aralkyloxy, —C(=O)—H, halogen, —C(=O)—OH, or —NO$_2$;
each R$^2$ and R$^3$ is independently H or alkyl;
R$^4$ is H, OR$^6$ or CH$_2$OR;
R$^5$ is H or CH$_2$OR;
R$^6$ is

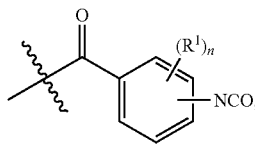

each X is independently —CH(CH$_3$)—C(=O)—O—; —(CH$_2$)$_y$—C(=O)—O—; or —(CH$_2$CH$_2$O)$_z$—CH$_2$—C(=O)—O—;
each Y is independently —O—C(=O)—CH(CH$_3$)—, —O—C(=O)—(CH$_2$)$_y$—, or —O—C(=O)—CH$_2$—(OCH$_2$CH$_2$)$_z$—;
each a and b is independently an integer from about 1 to about 6;
n is an integer from about 0 to about 4;
p is an integer from about 0 to about 10;
s is the integer 0 or 1; and
each y and z is independently an integer from about 1 to about 24.

In other embodiments, the present invention is directed to processes for preparing biocompatible and/or bioabsorbable polyisocyanate compounds of Formula I:

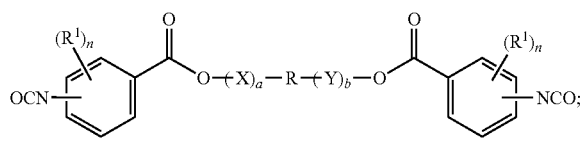

wherein:
R is alkylene-[C(R$^4$)(R$^5$)]$_s$-alkylene-, wherein:
   (1) one or more of the —CH$_2$— moieties in one or more alkylene chain portions of R are optionally replaced by —O— or —S—; or
   (2) one or more of the —CH$_2$—CH$_2$— moieties in the alkylene chain portions of R are optionally replaced by —C(=O)—O— or —O—C(=O)—;

each R$^1$ is independently [—C(R$^2$)(R$^3$)—]$_p$-Z;
each Z is independently alkoxy, aralkyloxy, —C(=O)—H, halogen, —C(=O)—OH, or —NO$_2$;
each R$^2$ and R$^3$ is independently H or alkyl;
R$^4$ is H, OR$^6$ or CH$_2$OR;
R$^5$ is H or CH$_2$OR;
R$^6$ is

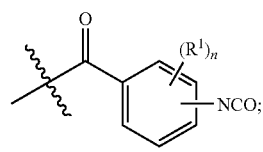

each X is independently —CH(CH$_3$)—C(=O)—O—; —(CH$_2$)$_y$—C(=O)—O—; or —(CH$_2$CH$_2$O)$_z$—CH$_2$—C(=O)—O—;
each Y is independently —O—C(=O)—CH(CH$_3$)—, —O—C(=O)—(CH$_2$)$_y$—, or —O—C(=O)—CH$_2$—(OCH$_2$CH$_2$)$_z$—;
each a and b is independently an integer from about 1 to about 6;
n is an integer from about 0 to about 4;
p is an integer from about 0 to about 10;
s is the integer 0 or 1; and
each y and z is independently an integer from about 1 to about 24; comprising contacting a diamine compound of Formula II:

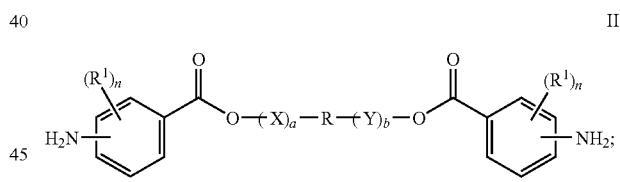

with an isocyanate forming agent; for a time and under conditions effective to provide the compound of Formula I.

DETAILED DESCRIPTION OF ILLUSTRATIVE EMBODIMENTS

The present invention generally relates to the discovery of novel uses for a class of biodegradable polyurethanes, polyureas, polyamideurethanes and/or polyureaurethanes derived from biocompatible and bioabsorbable polyisocyanates. The present invention is also related to novel processes for the manufacture of the biocompatible and bioabsorbable polyisocyanates. The bioabsorbable polymers that result from polymerization of the bioabsorbable polyisocyanates are useful for, inter alia, drug delivery, tissue engineering, and other implantable medical devices. In addition, these bioabsorbable polymers may have a controllable degradation profile.

As employed above and throughout the disclosure, the following terms, unless otherwise indicated, shall be understood to have the following meanings.

As used herein, "alkyl" refers to an optionally substituted, saturated straight, or branched hydrocarbon moiety having from about 1 to about 20 carbon atoms (and all combinations and subcombinations of ranges of carbon atoms and specific numbers of carbon atoms therein), preferably with from about 1 to about 8 carbon atoms, herein referred to as "lower alkyl", more preferably from about 1 to about 3 carbon atoms, with methyl or ethyl being even more preferred. Alkyl groups include, but are not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, and 2,3-dimethylbutyl.

As used herein, "alkylene" refers to a bivalent alkyl moiety having the general formula —$(CH_2)_n$—, where n is from about 1 to about 75, preferably about 1 to about 10, more preferably about 1 to about 8, with about 1 to about 5 being even more preferred. By bivalent, it is meant that the group has two open sites that each bond to another group. Non-limiting examples include methylene, ethylene, trimethylene, pentamethylene, and hexamethylene. Alkylene groups can be optionally substituted with alkyl, wherein alkyl is as previously defined. The term "lower alkylene" herein refers to those alkylene groups having from about 1 to about 6 carbon atoms.

As used herein, the term "aralkyl" refers to an optionally substituted ring system comprising an alkyl radical bearing an aryl substituent and having from about 7 to about 50 carbon atoms (and all combinations and subcombinations of ranges and specific numbers of carbon atoms therein), preferably with from about 7 to about 11 carbon atoms, with about 7 carbon atoms being preferred. Non-limiting examples include, for example, benzyl, diphenylmethyl, triphenylmethyl, phenylethyl, and diphenylethyl.

As used herein, the term "alkoxy" refers to an optionally substituted alkyl-O— group wherein alkyl is as previously defined. In some preferred embodiments, the alkyl moieties of the alkoxy groups have from about 1 to about 4 carbon atoms. Exemplary alkoxy groups include, but are not limited to, methoxy, ethoxy, n-propoxy, i-propoxy, n-butoxy, and heptoxy.

As used herein, the term "aralkoxy" refers to an optionally substituted aralkyl-O— group wherein aralkyl is as previously defined. Exemplary aralkoxy groups include, but are not limited to, benzyloxy, 1-phenylethoxy, 2-phenylethoxy, and 3-naphthylheptoxy. In certain preferred embodiments, aryloxy is benzyloxy.

As used herein, the term "reducing agent" refers to an agent, typically a reagent, capable of reducing functionality attached to an arene ring system, preferably wherein the functionality being reduced is a nitro (—$NO_2$) substituent directly attached to the arene ring system, more preferably wherein the nitro substituent is reduced to an amino (—$NH_2$) substituent. In certain preferred embodiments, the reducing agent is capable of reducing the nitro substituent to an amino substituent without substantially affecting other groups or moieties present in the compound being reduced. In certain preferred embodiments, the reducing agent is hydrogen, or its equivalent, in the presence of a catalyst. Numerous examples are known to those of ordinary skill in the art. See, for example, Richard C. Larock, "Comprehensive Organic Transformations", VCH Publishers, New York, 1989, pp 411-416; Jerry March, "Advanced Organic Chemistry", $4^{th}$ Ed., John Wiley and Sons, Inc., 1992, pp 446, 660, 1216-1218, 1223, and 1232-1233, the disclosures of which are hereby incorporated herein by reference, in their entireties.

As used herein, the term "bioabsorbable" refers to those classes of materials that readily react or enzymatically degrade upon exposure to bodily tissue for a relatively short period of time, thus experiencing a significant weight loss in that short time period. Complete bioabsorption should take place within twelve months, although preferably bioabsorption will be complete within nine months, and most preferably within six months. In this manner, the polymers derived from the polyisocyanates of the invention may be fabricated into medical and surgical devices which are useful for a vast array of applications requiring complete or substantially complete absorption within the relatively short time periods set forth herein.

The biological properties of the bioabsorbable polymers of the invention used to form devices or parts thereof, as measured by its absorption rate and its breaking strength retention in vivo (BSR), can be varied to suit the needs of the particular application for which the fabricated medical device or component is intended. This can be conveniently accomplished by varying the ratio of components of the polymer chosen.

Depending on the formation route selected, these cleavable sites may be regular along the length of the chain extender, thereby giving the segmented polyurethane a biodegradability which is, by some measure, predictable. Biodegradability is influenced by a number of factors, including crystallinity. The hydrophilicity of the polymer may also influence the degradability, that is, the extent to which water is accessible to the polymer matrix. The number of cleavage sites may also influence biodegradability. Generally speaking, the higher the number of sites, the greater the rate of degradation. Preferably, the cleavable site is an ester site and, more preferably, the cleavable ester site is derived from an hydroxy acid precursor. This provides segmented polyurethanes with cleavable sites that may be arranged to be recognizable by enzymes.

As used herein, the term "biodegradable wound or burn dressing" refers to the ability of at least some of the functional groups in the polymer chain comprising a wound or burn dressing to be hydrolyzed when the dressing is exposed to the physical elements of nature over a period of time.

As used herein, the term "partially biodegradable" refers to the percentage of functional groups in the polymer chain that are hydrolyzed as against the number of functional groups in the polymer chain initially present. In the context of a biodegradable wound or burn dressing, the term partially biodegradable refers to about 10%, preferably about 25%, more preferably about 40%, still more preferably about 60%, even more preferably about 75% hydrolysis of the functional groups initially present in the polymer chain of the wound or burn dressing.

When any variable occurs more than one time in any constituent or in any formula, its definition in each occurrence is independent of its definition at every other occurrence. Combinations of substituents and/or variables are permissible only if such combinations result in stable compounds. Within the context of the present invention, compounds are stable if they do not degrade significantly prior to their intended use under normal conditions. In some instances, compounds of the invention are may be designed or required to be bioabsorbed or biodegraded as part of their intended function. Bioabsorbability and/or biodegradability, which may be an advantageous property of the present polymers, is not intended to mean that the polymeric compound are unstable.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form, except where such limit is clearly defined.

Accordingly, the present invention is directed, in part, to surgical articles or components thereof comprising a polyurethane, polyurea, polyamideurethane or polyureaurethane derived from a biocompatible and/or bioabsorbable polyisocyanate of Formula Ib:

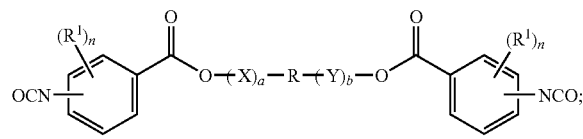

Ib wherein:

R is alkylene-$[C(R^4)(R^5)]_s$-alkylene-, wherein:
(1) one or more of the —$CH_2$— moieties in one or more alkylene chain portions of R are optionally replaced by —O— or —S—; or
(2) one or more of the —$CH_2$—$CH_2$— moieties in the alkylene chain portions of R are optionally replaced by —C(=O)—O— or —O—C(=O)—;

each $R^1$ is independently $[-C(R^2)(R^3)-]_p$-Z;

each Z is independently alkoxy, aralkyloxy, —C(=O)—H, halogen, —C(=O)—OH, or —$NO_2$;

each $R^2$ and $R^3$ is independently H or alkyl;

$R^4$ is H, alkyl, $(Y^1)_cOR^6$, $OR^6$, $CH_2$—$(Y^2)_dOR^6$, or $CH_2OR^6$;

$R^5$ is H, alkyl, $CH_2$—$(Y^2)_dOR^6$, or $CH_2OR^6$;

each $R^6$ is independently:

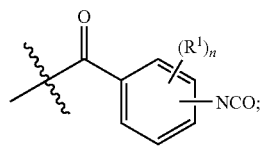

each X is independently —$CH(CH_3)$—C(=O)—O—, —$(CH_2)_y$—C(=O)—O—, or —$(CH_2CH_2O)_z$—$CH_2$—C(=O)—O—;

each Y, $Y^1$, and $Y^2$ is independently —O—C(=O)—CH($CH_3$)—, —O—C(=O)—$(CH_2)_y$-, or —O—C(=O)—$CH_2$—$(OCH_2CH_2)_z$—;

each a, b, c, and d is independently an integer from about 1 to about 6;

n is an integer from about 0 to about 4;

p is an integer from about 0 to about 10;

s is the integer 0 or 1; and each y and z is independently an integer from about 1 to about 24.

In other embodiments, the present invention is directed, in part, to surgical articles or components thereof comprising a polyurethane, polyurea, polyamideurethane or polyureaurethane derived from a biocompatible and/or bioabsorbable polyisocyanate of Formula I:

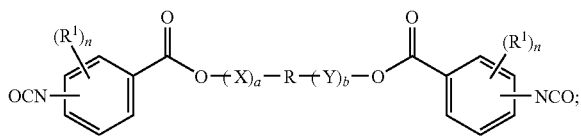

I wherein:

R is alkylene-$[C(R^4)(R^5)]_s$-alkylene-, wherein:
(1) one or more of the —$CH_2$— moieties in one or more alkylene chain portions of R are optionally replaced by —O— or —S—; or
(2) one or more of the —$CH_2$—$CH_2$— moieties in the alkylene chain portions of R are optionally replaced by —C(=O)—O— or —O—C(=O)—;

each $R^1$ is independently $[-C(R^2)(R^3)-]_p$-Z;

each Z is independently alkoxy, aralkyloxy, —C(=O)—H, halogen, —C(=O)—OH, or —$NO_2$;

each $R^2$ and $R^3$ is independently H or alkyl;

$R^4$ is H, $OR^6$ or $CH_2OR^6$;

$R^5$ is H or $CH_2OR^6$;

each $R^6$ is independently:

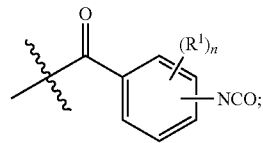

each X is independently —$CH(CH_3)$—C(=O)—O—, —$(CH_2)_y$—C(=O)—O—, or —$(CH_2CH_2O)_z$—$CH_2$—C(=O)—O—;

each Y is independently —O—C(=O)—CH($CH_3$)—, —O—C(=O)—$(CH_2)_y$—, or —O—C(=O)—$CH_2$—$(OCH_2CH_2)_z$—;

each a and b is independently an integer from about 1 to about 6;

n is an integer from about 0 to about 4;

p is an integer from about 0 to about 10;

s is the integer 0 or 1; and each y and z is independently an integer from about 1 to about 24.

In certain preferred embodiments, the polyisocyanate of Formula Ib employed in the surgical devices, pharmaceutical compositions, and/or prepared by the processes of manufacture has the structure of the polyisocyanate of Formula I:

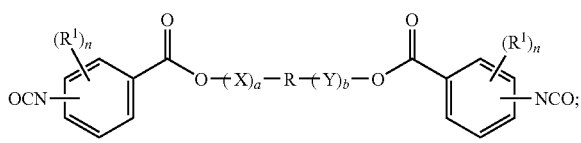

I wherein:

$R^1$, X, Y, a, b, and n are as defined hereinabove for the compounds of Formula I.

In certain more preferred embodiments, the polyisocyanate of Formula I employed in the surgical devices, pharmaceutical compositions, and/or prepared by the processes of manufacture has the structure of the polyisocyanate of Formula Ia:

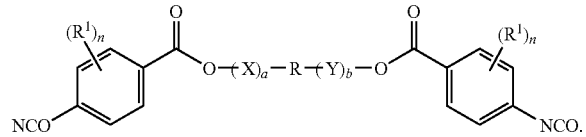

wherein $R^1$, X, Y, a, b, and n are as defined hereinabove for compounds of Formula I In certain other preferred embodiments, the polyisocyanate of Formula Ib employed in the surgical devices, pharmaceutical compositions, and/or prepared by the processes of manufacture has the structure Ic, Id, or Ie:

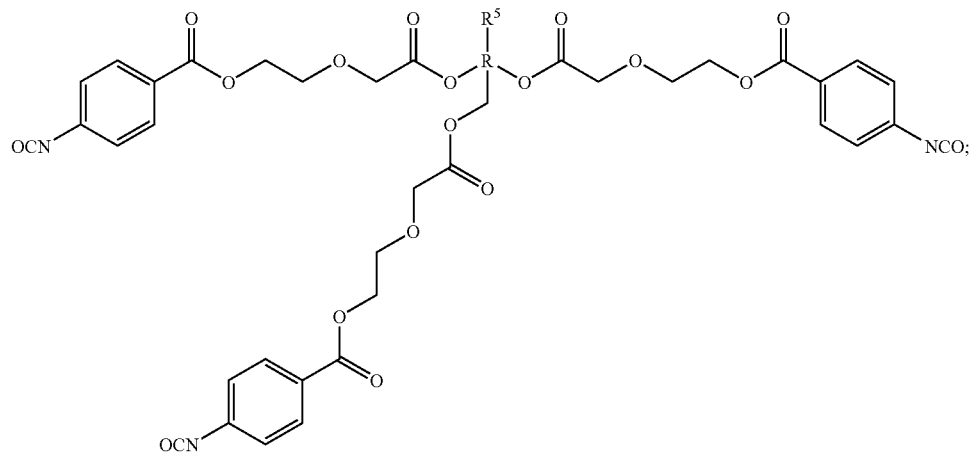

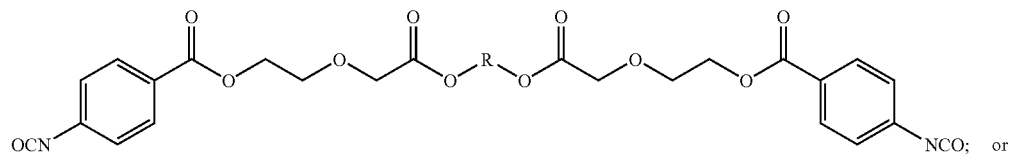

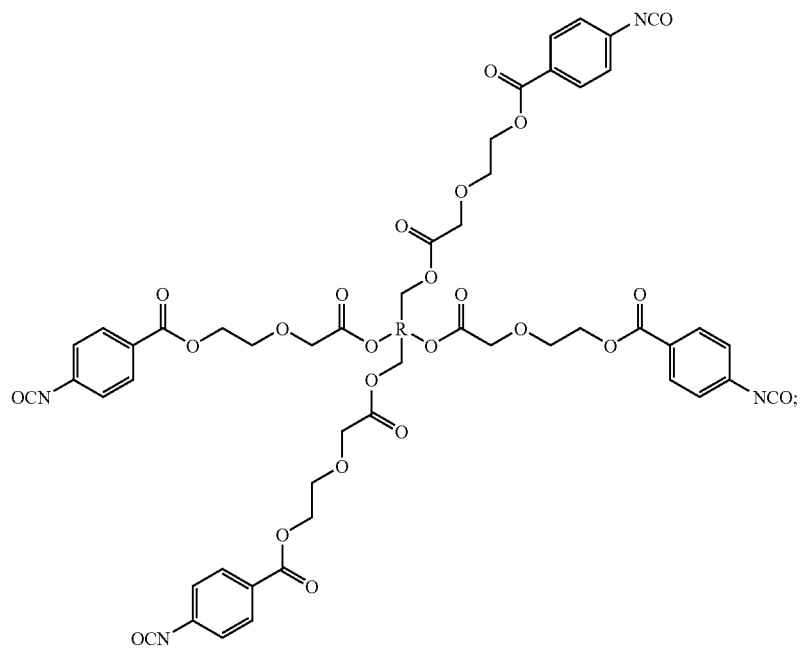

wherein R and R⁵ are as defined hereinabove. In certain preferred embodiments of Formula Ic, R⁵ is alkyl, preferably $C_{1-3}$alkyl, still more preferably ethyl. In other preferred embodiments of Formula Id, R is —CH₂CH₂CH₂—. In still other preferred embodiments of Formula Ic R is —CH₂C(H)(R⁵)CH₂—. In yet other preferred embodiments, R is —CH₂C(R⁴)(R⁵)CH₂—, wherein R⁴ and R⁵ are each independently CH₂—(Y²)$_d$OR⁶.

In other more preferred embodiments, the polyisocyanate of Formula I, Ia, or Ib employed in the surgical devices, pharmaceutical compositions, polymers, for example, polyurethanes, polyureas, polyamideurethanes and polyureaurethanes, and/or prepared by the processes of manufacture has the structure Id:

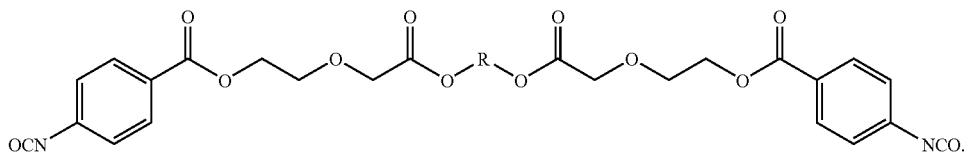

Id

In other embodiments, the invention is directed to pharmaceutical compositions comprising a polymeric carrier and a drug uniformly dispersed therein;
wherein the polymeric carrier comprises a polyurethane, polyurea, polyamideurethane and/or polyureaurethane derived from a biocompatible and bioabsorbable polyisocyanate of Formula Ib:

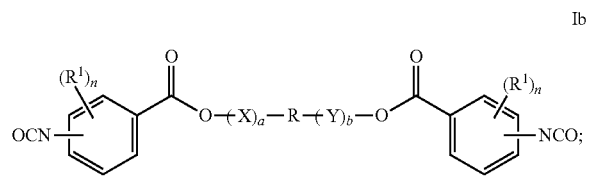

Ib wherein:
R is alkylene-[C(R⁴)(R⁵)]$_s$-alkylene-, wherein:
  (1) one or more of the —CH₂— moieties in one or more alkylene chain portions of R are optionally replaced by —O— or —S—; or
  (2) one or more of the —CH₂—CH₂— moieties in the alkylene chain portions of R are optionally replaced by —C(=O)—O— or —O—C(=O)—;
each R¹ is independently [—C(R²)(R³)—]$_p$-Z;
each Z is independently alkoxy, aralkyloxy, —C(=O)—H, halogen, —C(=O)—OH, or —NO₂;
each R² and R³ is independently H or alkyl;
R⁴ is H, alkyl, (Y¹)$_c$OR⁶, OR⁶, CH₂—(Y²)$_d$OR⁶, or CH₂OR⁶;
R⁵ is H, alkyl, CH₂—(Y²)$_d$OR⁶, or CH₂OR⁶;
each R⁶ is independently:

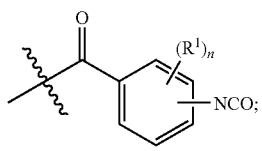

each X is independently —CH(CH₃)—C(=O)—O—, —(CH₂)$_y$—C(=O)—O—, or —(CH₂CH₂O)$_z$—CH₂—C(=O)—O—;
each Y, Y¹, and Y² is independently —O—C(=O)—CH(CH₃)—, —O—C(=O)—(CH₂)$_y$, or —O—C(=O)—CH₂—(OCH₂CH₂)$_z$—;
each a, b, c, and d is independently an integer from about 1 to about 6;
n is an integer from about 0 to about 4;
p is an integer from about 0 to about 10;
s is the integer 0 or 1; and
each y and z is independently an integer from about 1 to about 24.

In other embodiments, the invention is directed to pharmaceutical compositions comprising a polymeric carrier and a drug uniformly dispersed therein;
wherein the polymeric carrier comprises a polyurethane, polyurea, polyamideurethane and/or polyureaurethane derived from a biocompatible and bioabsorbable polyisocyanate of Formula I:

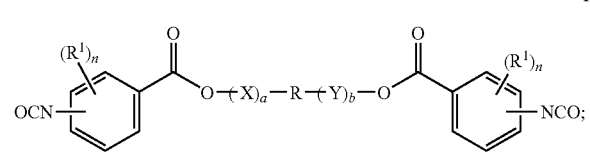

I wherein:
R is alkylene-[C(R⁴)(R⁵)]$_s$-alkylene-, wherein:
  (1) one or more of the —CH₂— moieties in one or more alkylene chain portions of R are optionally replaced by —O— or —S—; or
  (2) one or more of the —CH₂—CH₂— moieties in the alkylene chain portions of R are optionally replaced by —C(=O)—O— or —O—C(=O)—;
each R¹ is independently [—C(R²)(R³)—]$_p$-Z;
each Z is independently alkoxy, aralkyloxy, —C(=O)—H, halogen, —C(=O)—OH, or —NO₂;
each R² and R³ is independently H or alkyl;
R⁴ is H, OR⁶ or CH₂OR⁶;
R⁵ is H or CH₂OR⁶;
each R⁶ is independently:

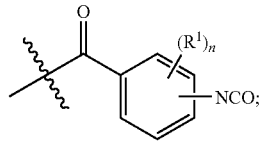

each X is independently —CH(CH₃)—C(=O)—O—, —(CH₂)$_y$—C(=O)—O—, or —(CH₂CH₂O)$_z$—CH₂—C(=O)—O—;

each Y is independently —O—C(=O)—CH(CH$_3$)—, —O—C(=O)—(CH$_2$)$_y$—, or —O—C(=O)—CH$_2$—(OCH$_2$CH$_2$)$_z$—;

each a and b is independently an integer from about 1 to about 6;

n is an integer from about 0 to about 4;

p is an integer from about 0 to about 10;

s is the integer 0 or 1; and each y and z is independently an integer from about 1 to about 24.

The present invention also relates to new methods of synthesis for polyisocyanates of Formula Ib from hydrolysable linkers of Formula Vb and nitrobenzoic acid derivatives of Formula IVb as shown in Scheme 1 below:

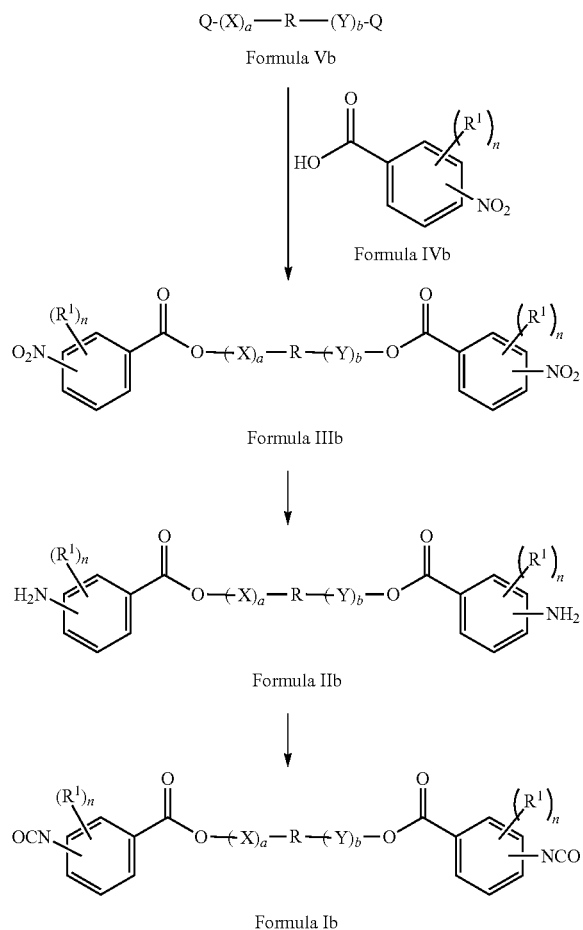

wherein:

R is alkylene-[C(R$^4$)(R$^5$)]$_s$-alkylene-, wherein:
(1) one or more of the —CH$_2$— moieties in one or more alkylene chain portions of R are optionally replaced by —O— or —S—; or
(2) one or more of the —CH$_2$—CH$_2$— moieties in the alkylene chain portions of R are optionally replaced by —C(=O)—O— or —O—C(=O)—;

each R$^1$ is independently [—C(R$^2$)(R$^3$)—]$_p$-Z;

each Z is independently alkoxy, aralkyloxy, —C(=O)—H, halogen, —C(=O)—OH, or —NO$_2$;

each R$^2$ and R$^3$ is independently H or alkyl;

R$^4$ is H, alkyl, (Y$^1$)$_c$OR$^6$, OR$^6$, CH$_2$—(Y$^2$)$_d$OR$^6$, or CH$_2$OR$^6$;

R$^5$ is H, alkyl, CH$_2$—(Y$^2$)$_d$OR$^6$, or CH$_2$OR$^6$;

each R$^6$ is independently:

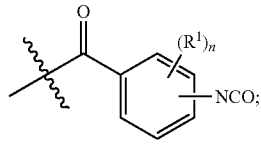

each X is independently —CH(CH$_3$)—C(=O)—O—, —(CH$_2$)$_y$—C(=O)—O—, or —(CH$_2$CH$_2$O)$_z$—CH$_2$—C(=O)—O—;

each Y, Y$^1$, and Y$^2$ is independently —O—C(=O)—CH(CH$_3$)—, —O—C(=O)—(CH$_2$)$_y$, or —O—C(=O)—CH$_2$—(OCH$_2$CH$_2$)$_z$—;

each a, b, c, and d is independently an integer from about 1 to about 6;

n is an integer from about 0 to about 4;

p is an integer from about 0 to about 10;

s is the integer 0 or 1; and each y and z is independently an integer from about 1 to about 24.

Accordingly, the present invention is directed, in part, to processes for preparing biocompatible and/or bioabsorbable polyisocyanate compounds of Formula Ib:

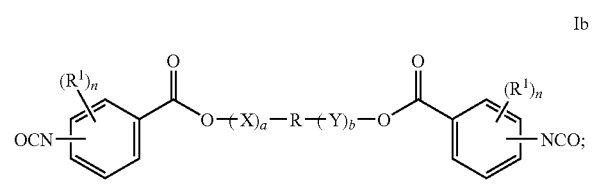

wherein:

R is alkylene-[C(R$^4$)(R$^5$)]$_s$-alkylene-, wherein:
(1) one or more of the —CH$_2$— moieties in one or more alkylene chain portions of R are optionally replaced by —O— or —S—; or
(2) one or more of the —CH$_2$—CH$_2$— moieties in the alkylene chain portions of R are optionally replaced by —C(=O)—O— or —O—C(=O)—;

each R$^1$ is independently [—C(R$^2$)(R$^3$)—]$_p$-Z;

each Z is independently alkoxy, aralkyloxy, —C(=O)—H, halogen, —C(=O)—OH, or —NO$_2$;

each R$^2$ and R$^3$ is independently H or alkyl;

R$^4$ is H, alkyl, (Y$^1$)$_c$OR$^6$, OR$^6$, CH$_2$—(Y$^2$)$_d$OR$^6$, or CH$_2$OR$^6$;

R$^5$ is H, alkyl, CH$_2$—(Y$^2$)$_d$OR$^6$, or CH$_2$OR$^6$;

each R$^6$ is independently:

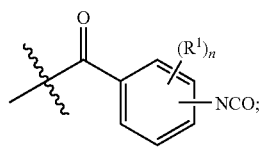

each X is independently —CH(CH$_3$)—C(=O)—O—, —(CH$_2$)$_y$—C(=O)—O—, or —(CH$_2$CH$_2$O)$_z$—CH$_2$—C(=O)—O—;

each Y, $Y^1$, and $Y^2$ is independently —O—C(=O)—CH(CH$_3$)—, —O—C(=O)—(CH$_2$)$_y$, or —O—C(=O)—CH$_2$—(OCH$_2$CH$_2$)$_z$—;

each a, b, c, and d is independently an integer from about 1 to about 6;

n is an integer from about 0 to about 4;

p is an integer from about 0 to about 10;

s is the integer 0 or 1; and each y and z is independently an integer from about 1 to about 24;

comprising contacting a diamine compound of Formula IIb:

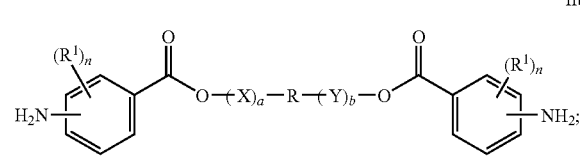

IIb with an isocyanate forming agent, preferably triphosgene; for a time and under conditions effective to provide the compound of Formula Ib.

In some other embodiments, the present invention is directed to processes for preparing biocompatible and/or bioabsorbable polyisocyanate compounds of Formula I:

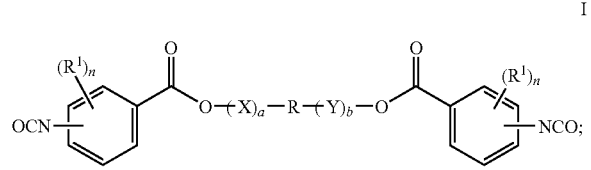

I wherein:

R is alkylene-[C(R$^4$)(R$^5$)]$_s$-alkylene-, wherein:
  (1) one or more of the —CH$_2$— moieties in one or more alkylene chain portions of R are optionally replaced by —O— or —S—; or
  (2) one or more of the —CH$_2$—CH$_2$— moieties in the alkylene chain portions of R are optionally replaced by —C(=O)—O— or —O—C(=O)—;

each $R^1$ is independently [—C(R$^2$)(R$^3$)—]$_p$-Z;

each Z is independently alkoxy, aralkyloxy, —C(=O)—H, halogen, —C(=O)—OH, or —NO$_2$;

each $R^2$ and $R^3$ is independently H or alkyl;

$R^4$ is H, OR$^6$ or CH$_2$OR;

$R^5$ is H or CH$_2$OR;

each $R^6$ is independently:

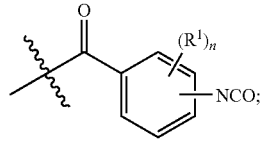

each X is independently —CH(CH$_3$)—C(=O)—O—, —(CH$_2$)$_y$—C(=O)—O—, or —(CH$_2$CH$_2$O)$_z$—CH$_2$—C(=O)—O—;

each Y is independently —O—C(=O)—CH(CH$_3$)—, —O—C(=O)—(CH$_2$)$_y$—, or —O—C(=O)—CH$_2$—(OCH$_2$CH$_2$)$_z$—;

each a and b is independently an integer from about 1 to about 6;

n is an integer from about 0 to about 4;

p is an integer from about 0 to about 10;

s is the integer 0 or 1; and each y and z is independently an integer from about 1 to about 24; comprising contacting a diamine compound of Formula II:

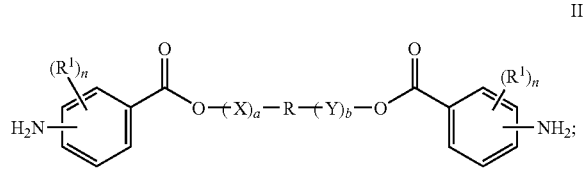

II with an isocyanate forming agent, preferably triphosgene;

for a time and under conditions effective to provide the compound of Formula I.

In some preferred embodiments directed to processes for preparing biocompatible and/or bioabsorbable polyisocyanate compounds of Formula I or Ib, the biocompatible and/or bioabsorbable polyisocyanate compounds being prepared have the following Formula Ia:

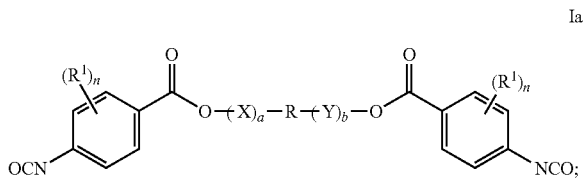

Ia wherein $R^1$, X, Y, a, b, and n are as defined hereinabove for compounds of Formula I and/or Ia.

In some preferred processes of the invention directed to preparing biocompatible and/or bioabsorbable polyisocyanate compounds of Formula Ib, the compound of Formula IIb is prepared by a process comprising contacting a compound of Formula IIIb:

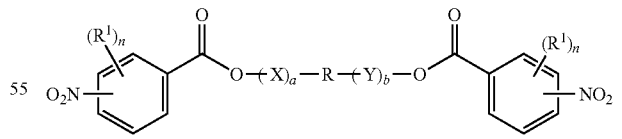

IIIb with a reducing agent for a time and under conditions effective to provide the compound of Formula IIb, wherein $R^1$, X, Y, a, b, and n are as defined hereinabove for compounds of Formula Ib.

In other preferred processes of the invention directed to preparing biocompatible and/or bioabsorbable polyisocyanate compounds of Formula I, the compound of Formula II is prepared by a process comprising contacting a compound of Formula III:

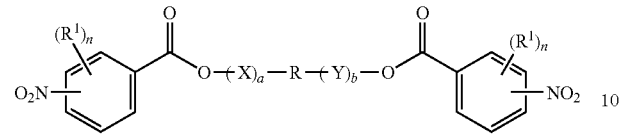

III with a reducing agent for a time and under conditions effective to provide the compound of Formula II, wherein $R^1$, X, Y, a, b, and n are as defined hereinabove for compounds of Formula I.

In certain more preferred processes of the invention directed to preparing biocompatible and/or bioabsorbable polyisocyanate compounds of Formula Ib or Formula I, the compound of Formula IIb or Formula II being prepared has the following Formula Ia:

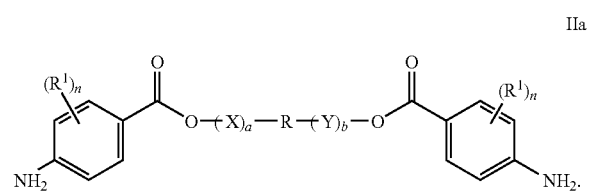

IIa

The compound of Formula Ia is preferably prepared by a process comprising contacting the corresponding nitro compound with a reducing agent for a time and under conditions effective to provide the compound of Formula Ia; wherein $R^1$, X, Y, a, b, and n are as defined hereinabove for compounds of Formula I or Ia.

In other preferred processes of the invention, the compound of Formula IIIb is prepared by a process comprising contacting a compound of Formula IVb:

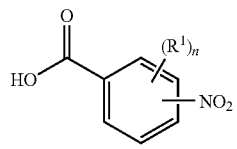

IVb with a compound of Formula Vb:

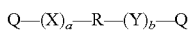

Vb for a time and under conditions effective to provide the compound of Formula IIIb;
wherein
each Q is independently F, Cl, Br, or I; and
$R^1$, X, Y, a, b, and n are as defined hereinabove for compounds of Formula Ib.

In other preferred processes of the invention, the compound of Formula III is prepared by a process comprising contacting a compound of Formula IV:

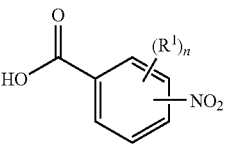

IV with a compound of Formula V:

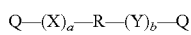

V for a time and under conditions effective to provide the compound of Formula III;
wherein
each Q is independently F, Cl, Br, or I; and
wherein $R^1$, X, Y, a, b, and n are as defined hereinabove for compounds of Formula I.

In certain more preferred processes of the invention, the compound of Formula III or Formula IIIb being prepared has the following Formula IIIa:

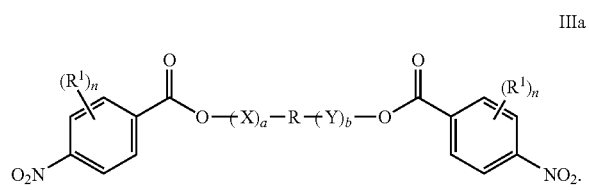

IIIa

The compound of Formula IIIa (para-nitro isomer) is prepared by a process comprising contacting a compound of Formula IVa:

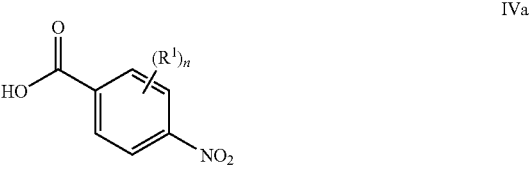

IVa with a compound of Formula Va:

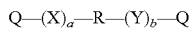

Va for a time and under conditions effective to provide the compound of Formula IIIa;
wherein
each Q is independently F, Cl, Br, or I; and
$R^1$, X, Y, a, b, and n are as defined hereinabove for compounds of Formula I.

The present invention is also directed to polyurethanes, polyureas, polyamideurethanes and polyureaurethanes which are derived from at least one polyisocyanate compound of Formula Ib:

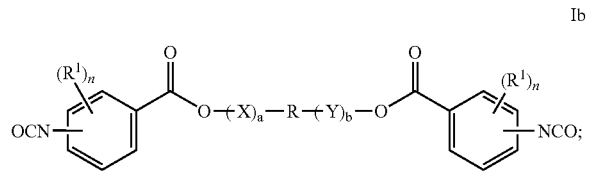

Ib wherein:
R is alkylene-[C(R$^4$)(R$^5$)]$_s$-alkylene-, wherein:
  (1) one or more of the —CH$_2$— moieties in one or more alkylene chain portions of R are optionally replaced by —O— or —S—; or
  (2) one or more of the —CH$_2$—CH$_2$— moieties in the alkylene chain portions of R are optionally replaced by —C(=O)—O— or —O—C(=O)—;
each R$^1$ is independently [—C(R$^2$)(R$^3$)—]$_p$-Z;
each Z is independently alkoxy, aralkyloxy, —C(=O)—H, halogen, —C(=O)—OH, or —NO$_2$;
each R$^2$ and R$^3$ is independently H or alkyl;
R$^4$ is H, alkyl, (Y$^1$)$_c$OR$^6$, OR$^6$, CH$_2$—(Y$^2$)$_d$OR$^6$, or CH$_2$OR$^6$;
R$^5$ is H, alkyl, CH$_2$—(Y$^2$)$_d$OR$^6$, or CH$_2$OR$^6$;
each R$^6$ is independently:

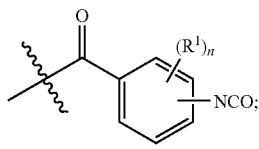

each X is independently —CH(CH$_3$)—C(=O)—O—, —(CH$_2$)$_y$—C(=O)—O—, or —(CH$_2$CH$_2$O)$_z$—CH$_2$—C(=O)—O—;
each Y, Y$^1$, and Y$^2$ is independently —O—C(=O)—CH(CH$_3$)—, —O—C(=O)—(CH$_2$)$_y$, or —O—C(=O)—CH$_2$—(OCH$_2$CH$_2$)$_z$—;
each a, b, c, and d is independently an integer from about 1 to about 6;
n is an integer from about 0 to about 4;
p is an integer from about 0 to about 10;
s is the integer 0 or 1; and
each y and z is independently an integer from about 1 to about 24.

In other embodiments, the present invention is directed to polyurethanes, polyureas, polyamideurethanes and polyureaurethanes which are derived from at least one polyisocyanate compound of Formula I:

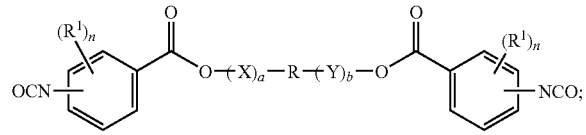

I wherein:
R is alkylene-[C(R$^4$)(R$^5$)]$_s$-alkylene-, wherein:
  (1) one or more of the —CH$_2$— moieties in one or more alkylene chain portions of R are optionally replaced by —O— or —S—; or
  (2) one or more of the —CH$_2$—CH$_2$— moieties in the alkylene chain portions of R are optionally replaced by —C(=O)—O— or —O—C(=O)—;
each R$^1$ is independently [—C(R$^2$)(R$^3$)—]$_p$-Z;
each Z is independently alkoxy, aralkyloxy, —C(=O)—H, halogen, —C(=O)—OH, or —NO$_2$;
each R$^2$ and R$^3$ is independently H or alkyl;
R$^4$ is H, OR$^6$ or CH$_2$OR;
R$^5$ is H or CH$_2$OR;
each R$^6$ is independently:

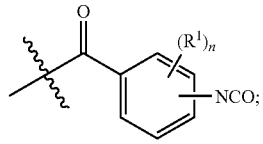

each X is independently —CH(CH$_3$)—C(=O)—O—, —(CH$_2$)$_y$—C(=O)—O—, or —(CH$_2$CH$_2$O)$_z$—CH$_2$—C(=O)—O—;
each Y is independently —O—C(=O)—CH(CH$_3$)—, —O—C(=O)—(CH$_2$)$_y$, or —O—C(=O)—CH$_2$—(OCH$_2$CH$_2$)$_z$—;
each a and b is independently an integer from about 1 to about 6;
n is an integer from about 0 to about 4;
p is an integer from about 0 to about 10;
s is the integer 0 or 1; and
each y and z is independently an integer from about 1 to about 24.

In some preferred embodiments, the polyurethanes, polyureas, polyamideurethanes, polyureaurethanes, and/or their polyisocyanate precursors of Formula I, Ia, or Ib have tunable physical and/or biological properties.

In some other more preferred embodiments, the compounds of Formula II have the Formula Ia:

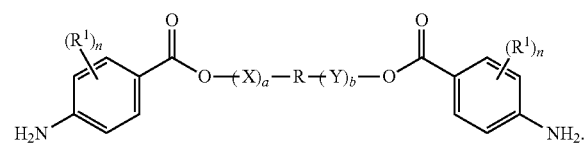

IIa

In certain other more preferred embodiments, the compounds of Formula III have the Formula IIIa:

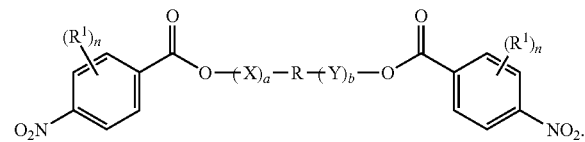

IIIa

In certain other more preferred embodiments, the compounds of Formula IV have the Formula IVa:

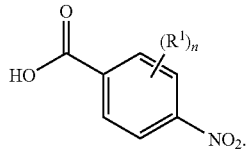

Iva

In other preferred embodiments of compounds of the Formula I, Ia, Ib, II, Ia, IIb, III, IIIa, IIIb, V, Va, or Vb, each alkylene moiety of R is independently C$_1$-C$_{50}$, preferably $C_1$-$C_{30}$, more preferably $C_1$-$C_{10}$, even more preferably $C_1$-$C_8$, still more preferably $C_1$-$C_6$, yet more preferably $C_1$-$C_4$alkylene. Alternatively, the alkylene is independently preferably $C_1$, $C_3$, $C_4$, or $C_8$alkylene. Also in preferred embodiments, the alkylene is unsubstituted or substituted with alkyl, preferably $C_1$-$C_3$alkyl, more preferably methyl. In other preferred embodiments wherein one or more —($CH_2$)— moieties in the alkylene chain portion of R are replaced with a heteroatom, preferably —O— or —S—, with —O— being more preferred. Preferably, one or more —($CH_2$)— moieties in an alkylene chain portion of R are replaced with from about 1 to about 25 —O— or —S— atoms, more preferably from about 5 to about 25 —O— or —S— atoms. In other alternative embodiments, wherein one or more —($CH_2$)-moieties in an alkylene chain portion of R are replaced, they are preferably replaced with from about 1 to about 5 —O— or —S— atoms, more preferably from about 1 to about 3 —O— or —S— atoms, still more preferably from about 1 to about 2 —O— or —S— atoms. Alternatively preferred in some embodiments, R is a polyol, such as for example, polyethylene glycol.

In some other preferred embodiments of the compounds of Formula I, Ia, Ib, II, Ia, IIb, III, IIIa, IIIb, V, Va, or Vb, wherein one or more —($CH_2CH_2$)— moieties in an alkylene chain portion of R are replaced, they are preferably replaced with from about 1 to about 10 —O—C(=O)— or —C(=O)—O— moieties, more preferably from about 1 to about 8 —O—C(=O)— or —C(=O)—O—moieties, still more preferably from about 1 to about 6 —O—C(=O)— or —C(=O)—O— moieties, with from about 1 to about 3 —O—C(=O)— or —C(=O)—O— moieties being even more preferred.

In some preferred embodiments of compounds of Formula I, Ia, Ib, II, Ia, IIb, III, IIIa, IIIb, V, Va, or Vb, s is 1. In alternate preferred embodiments, s is 0.

In other preferred embodiments of compounds of Formula I, Ia, Ib, II, Ia, IIb, III, IIIa, IIIb, V, Va, or Vb, each $R^1$ is independently Z.

In yet other preferred embodiments of the compounds of Formula I, Ia, Ib, II, Ia, IIb, III, IIa, IIIb, V, Va, or Vb, each Z is independently alkoxy, aralkyloxy, —C(=O)—H, halogen, —C(=O)—OH, or —$NO_2$. In embodiments wherein Z is aralkyloxy, it is preferably benzyloxy.

In certain preferred embodiments of the compounds of Formula I, Ia, Ib, II, Ia, IIb, III, IIa, IIIb, V, Va, or Vb, each $R^2$ and $R^3$ is independently H or alkyl, more preferably H. In some embodiments wherein $R^2$ and $R^3$ is alkyl, it is preferably $C_1$-$C_3$alkyl, more preferably methyl.

In some preferred embodiments of the compounds of Formula I, Ia, Ib, II, Ia, IIb, III, IIIa, IIIb, V, Va, or Vb, $R^4$ is $OR^6$ or $CH_2OR^6$. In other embodiments, $R^4$ is preferably H. Alternatively preferred, $R^4$ is alkyl. In other preferred embodiments, $R^4$ is $(Y^1)_cOR^6$ or $CH_2$—$(Y^2)_dOR^6$, with $CH_2$—$(Y^2)_d OR^6$ being even more preferred.

In some other preferred embodiments of the compounds of Formula I, Ia, Ib, II, Ia, IIb, III, IIIa, IIIb, V, Va, or Vb, $R^5$ is $CH_2OR^6$. In other preferred embodiments, $R^5$ is H. Alternatively preferred, $R^5$ is $CH_2$—$(Y^2)_d OR^6$ In certain preferred embodiments of the compounds of Formula I, Ia, or Ib, each $R^6$ is independently:

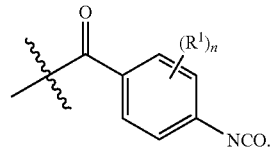

In still other preferred embodiments of the compounds of Formula I, Ia, Ib, II, Ia, IIb, III, IIIa, IIIb, V, Va, or Vb, each X is independently —CH($CH_3$)—C(=O)—O—, —($CH_2$)$_y$—C(=O)—O—. In other preferred embodiments, each X is independently —($CH_2CH_2O$)$_z$—$CH_2$—C(=O)—O—. In alternate preferred embodiments, each X is independently —CH($CH_3$)—C(=O)—O—, —($CH_2$)—C(=O)—O—, —($CH_2$)$_5$—C(=O)—O— or —$CH_2CH_2$O—$CH_2$—C(=O)—O—.

In still other preferred embodiments of the compounds of Formula I, Ia, Ib, II, Ia, IIb, III, IIIa, IIIb, V, Va, or Vb, each Y, $Y^1$, and $Y^2$ is independently —O—C(=O)—CH($CH_3$)— or —O—C(=O)—($CH_2$)$_y$—. In other preferred embodiments; each Y, $Y^1$, and $Y^2$ is independently —O—C(=O)—$CH_2$—(O$CH_2CH_2$)$_z$—. In alternate preferred embodiments, each Y, $Y^1$, and $Y^2$ is independently —O—C(=O)—CH($CH_3$)—, —O—C(=O)—($CH_2$)—, —O—C(=O)—($CH_2$)$_5$—, or —O—C(=O)—$CH_2OCH_2CH_2$—.

In certain preferred embodiments of the compounds of Formula I, Ia, Ib, II, Ia, IIb, III, IIIa, IIIb, V, Va, or Vb, each a, b, c, and d is independently an integer from about 1 to about 6, preferably about 1 to about 4, more preferably about 1 to about 3. In alternate preferred embodiments, each a, b, c, and d is independently an integer from about 2 to about 6, preferably about 2 to about 4, more preferably about 2 to about 3. In certain alternative preferred embodiments, each a, b, c, and d is independently an integer is 1 or 2, more preferably 1. In other alternative embodiments, each d is independently 1 or 2, preferably 1.

In some preferred embodiments of the compounds of Formula I, Ia, Ib, II, Ia, IIb, III, IIIa, IIIb, V, Va, or Vb, each y and z is independently an integer from about 1 to about 24, more preferably from about 1 to about 18, still more preferably from about 1 to about 12, yet more preferably from about 1 to about 8, even more preferably from about 1 to about 6. In certain alternative preferred embodiments, each y and z is independently 1 or 5.

In some preferred embodiments of the compounds of Formula I, Ia, Ib, II, Ia, IIb, III, IIIa, IIIb, V, Va, or Vb, each n is an integer from about 0 to about 4; more preferably about 0 to about 2, still more preferably from about 0 to about 1, with 0 being even more preferred.

In some preferred embodiments of the compounds of Formula I, Ia, Ib, II, Ia, IIb, III, IIIa, IIIb, V, Va, or Vb, p is from about 0 to about 2, more preferably from about 0 to about 1, still more preferably 0.

Suitable examples of polyisocyanates of Formula I, Ia, or Ib that may be used to prepare polyurethanes of the present invention for applications as stents, stent coatings, films, scaffolds and polyurethane foams include but are not limited to the exemplary compounds shown below:

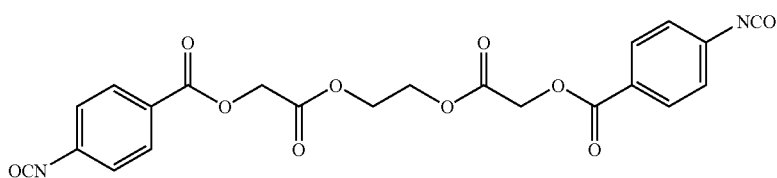
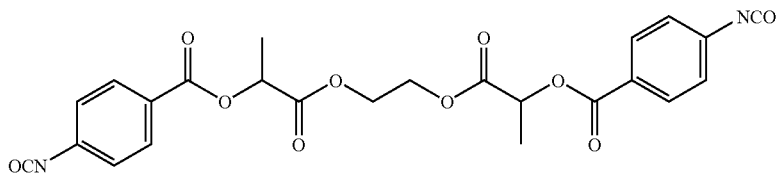
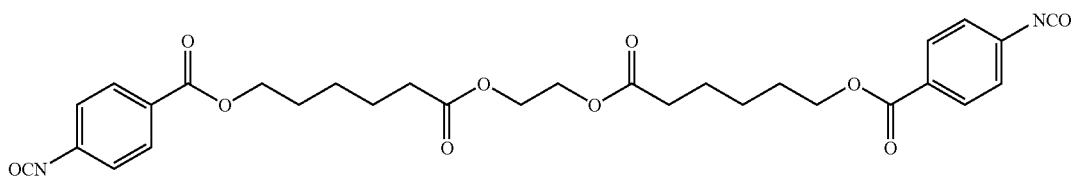
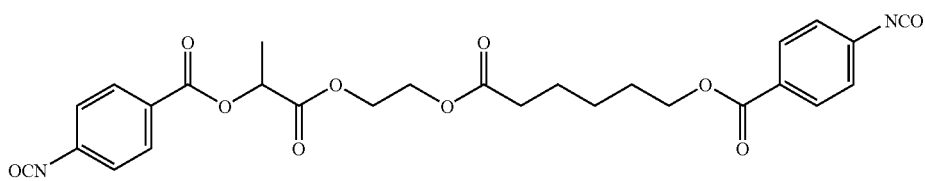
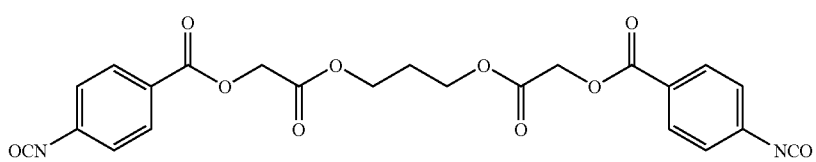
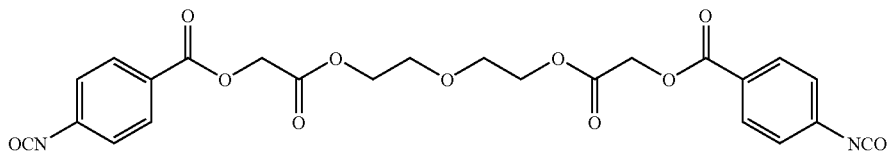
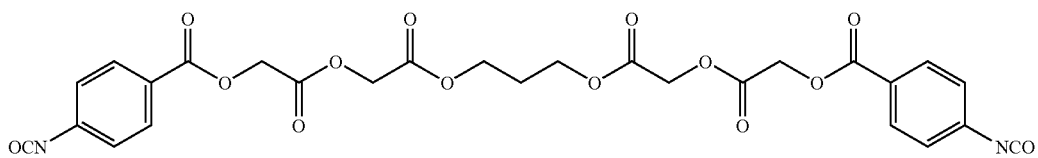
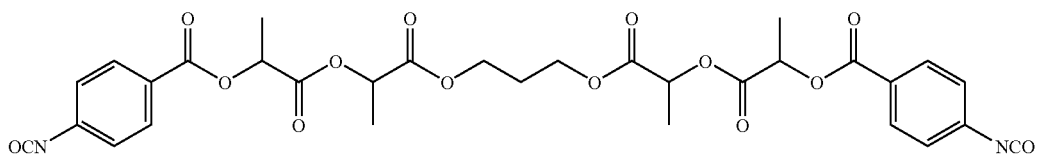
In other embodiments, polyurethanes, polyureas, polyureaurethanes, and polyamide urethanes of the present invention, particularly in connection with their use as stents, stent coatings, films, scaffolds and polyurethane foams, may be derived from multi-armed polyisocyanates including but not limited to the exemplary polyisocyanates shown below:

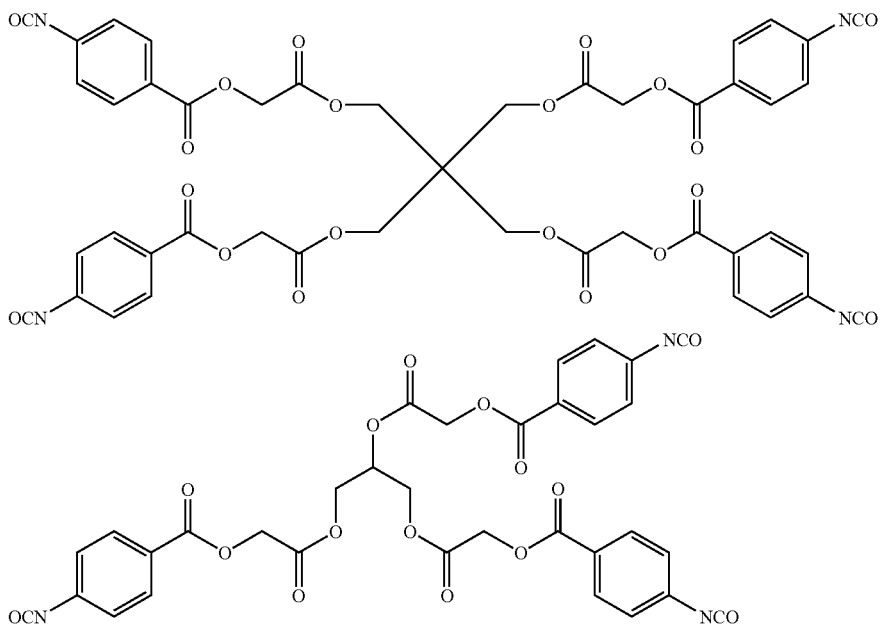

Polyols that may be suitable for use in the preparation of polyurethanes, polyureas, polyureaurethanes, and polyamideurethanes of the present invention include but are not limited to diols and polydiols having repeating units containing up to about 18 carbon atoms. Examples of suitable diols include 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,8-octanediol and combinations thereof. Examples of preferred polydiols include polyethylene glycol with molecular weights of from about 500 to about 10000, polytetramethylene ether glycols, polyols derived from glycolide, lactide, trimethylenecarbonate, p-dioxanone and/or caprolactone with molecular weights of about 500 to about 10000.

Amines including diamines that may be suitable for use in the preparation of polyurea and polyureaurethanes of the present invention include but are not limited to polyethyleneimines, PEG amines with weight average molecular weights from about 500 to about 5,000, polyoxypropylenediamines available under the tradename JEFFAMINES (Huntsman Corporation, Houston, Tex.), spermine, spermidine, hexamethylenediamine, octamethylenediamine, decamethylenediamine, dodecamethylenediamine, hexadecamethylenediamine, octadecamethylenediamine, polyamidoamine dendrimers, dextrans, PEG-dextran conjugates, cysteines, proteins containing amines, non-biologically active symmetrical and unsymmetrical diamino compounds containing saturated and unsaturated, substituted and unsubstituted alkyl, aryl and alkylaryl groups having from about 2 to about 18 carbon atoms and hydrolysable diamines having the following formulas.

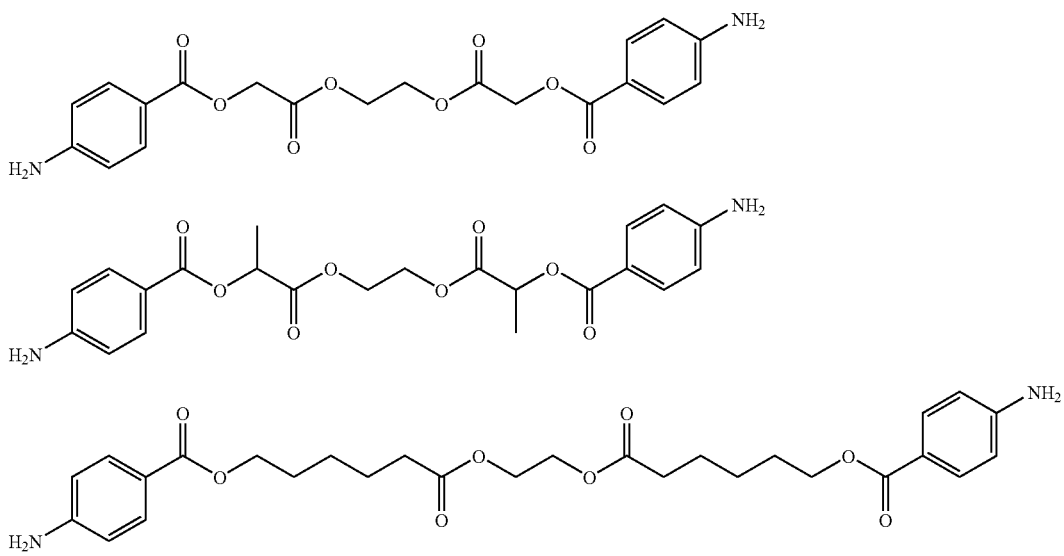

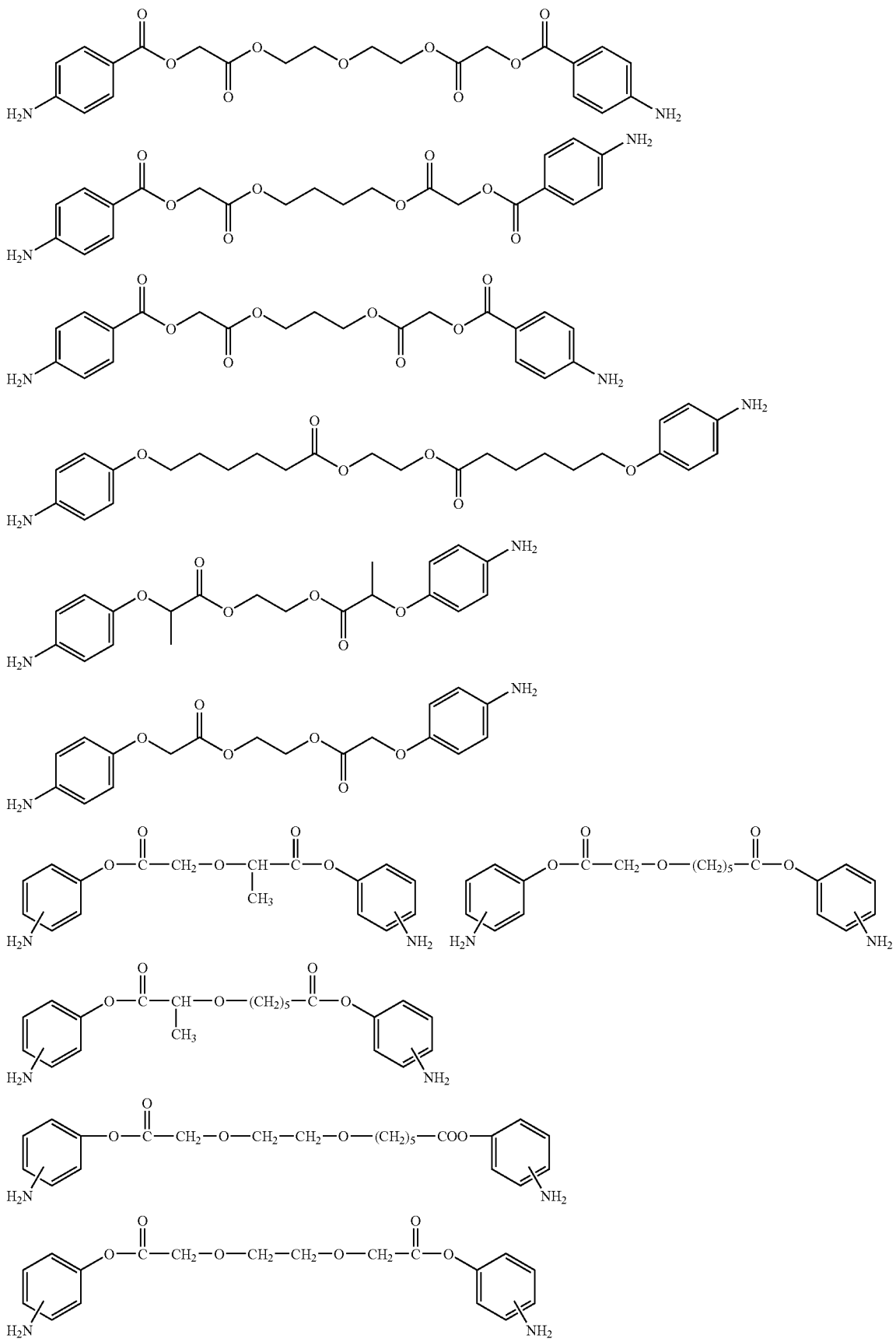

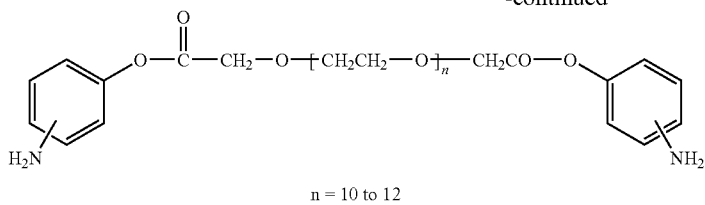
n = 10 to 12
Amide diols that may be suitable for use in the preparation of polyamideurethanes of the present invention include but are not limited to compounds having the following formulas.
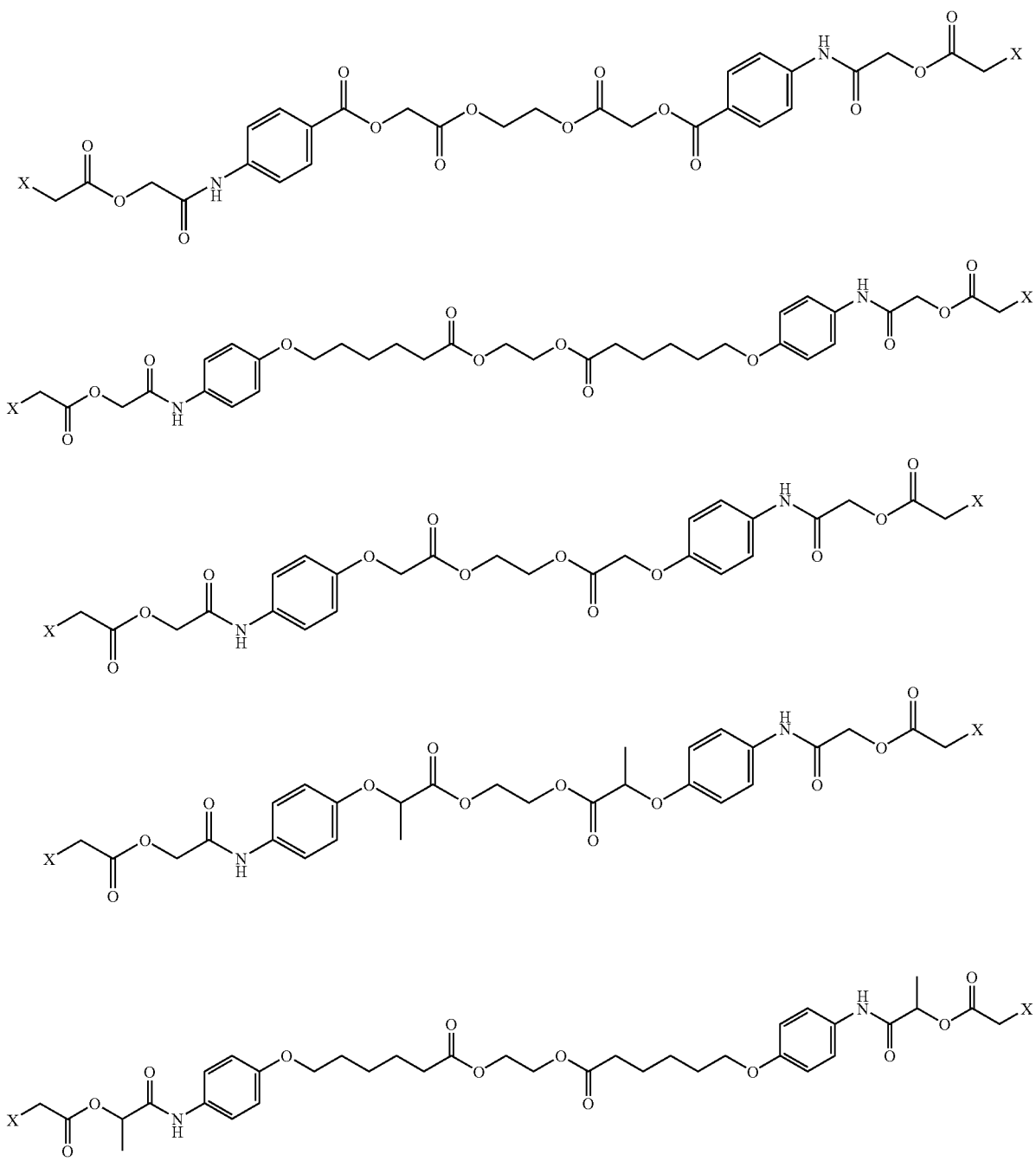

-continued

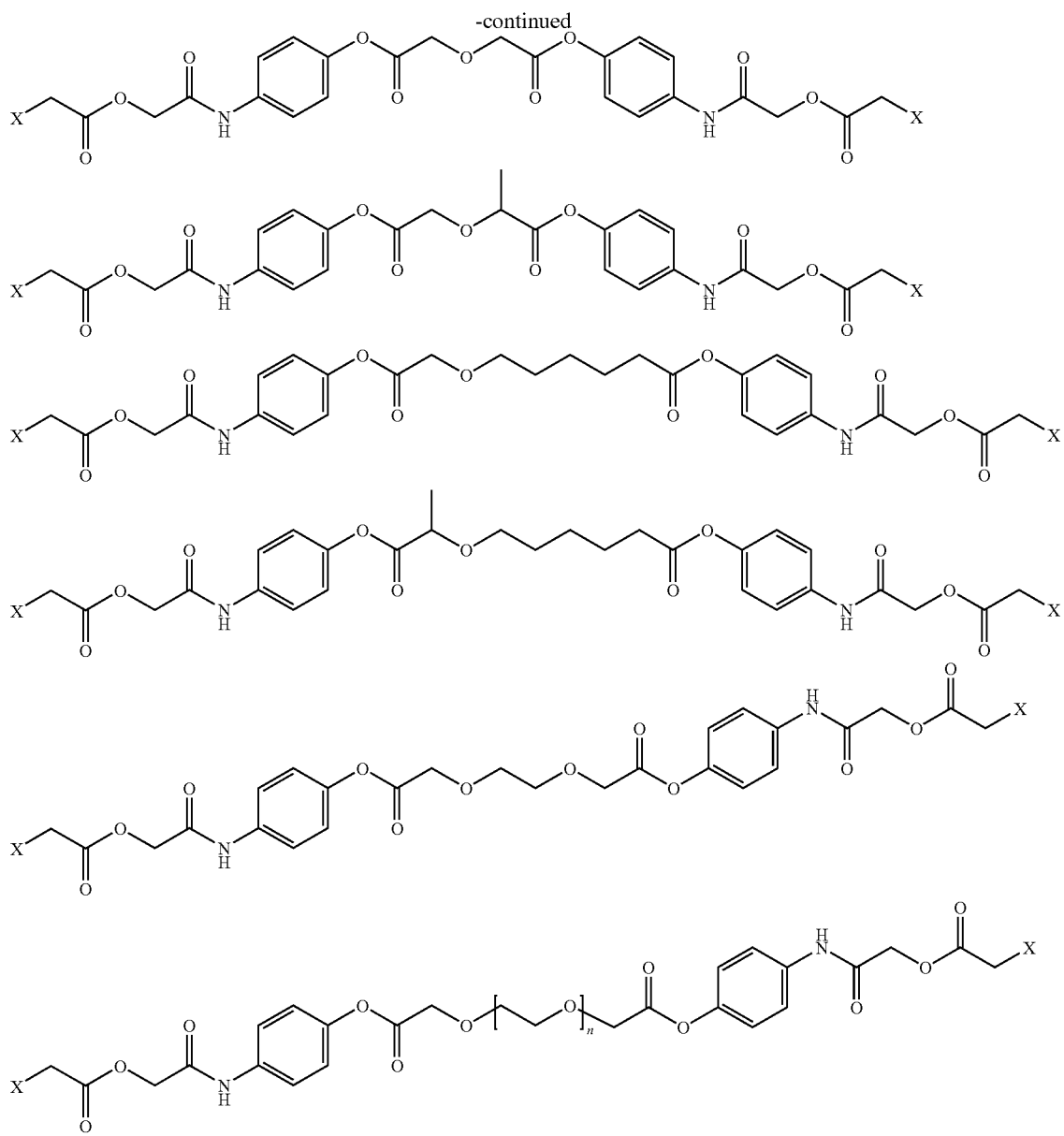

n = 10 - 12 wherein X is OH

It would be readily apparent to one of ordinary skill in the art once armed with the teachings in the present application that the polyisocyanates of the present invention may be reacted with a variety of reactants that are typically employed in the preparation of bioabsorbable and biocompatible polyurethanes, polyureas, polyamideurethanes, and/or polyureaurethanes, preferably with tunable physical, mechanical properties and/or hydrolytic degradation profiles. It would also be apparent to the ordinarily skilled artisan that the terminal groups for a given polyurethane, polyurea, polyamideurethane and/or polyureaurethane may be derivatized by further reacting the polyurethane, polyurea, polyamideurethane and/or polyureaurethane with additional derivatizing agents.

In certain preferred embodiments, the polyurethane, polyurea, polyamideurethane and/or polyureaurethane as described herein may be further polymerized with a lactone monomer, preferably selected from the group consisting of glycolide, lactide, ε-caprolactone, trimethylene carbonate, and p-dioxanone. In certain preferred embodiments, the surgical articles of the present invention comprise these further polymerized polyurethanes, polyureas, polyamideurethanes and/or polyureaurethanes.

In preferred form, the polyurethanes, polyureas, polyamideurethanes and/or polyureaurethanes described herein are biodegradable and in certain aspects biocompatible and suitable for use in medicine. Such polyurethanes, polyureas, polyamideurethanes and/or polyureaurethanes combine the good mechanical properties of polyurethanes, polyureas, polyamideurethanes and/or polyureaurethanes with the degradability of polyesters.

The degradable polyurethane, polyurea, polyamideurethane, and/or polyureaurethane herein is suitable for use in a wide variety of applications. Since the degradation products of the biocompatible polyurethanes, polyureas, polyamideurethanes, and/or polyureaurethanes described herein are non-toxic, they are advantageously suitable for biomedical uses. For example, the properties of the polymer may be tunable, i.e., they may be made to degrade more slowly or more quickly by reducing or increasing respectively the number of ester linkages in the polymeric chain, and can thus be utilized for fabricating short-term or long-term implantable surgical materials.

The polyurethanes, polyureas, polyamideurethanes, and/or polyureaurethanes may be formed into surgical articles using any known technique, such as, for example, extrusion, molding and/or solvent casting. The polyurethanes, polyureas, polyamideurethanes, and/or polyureaurethanes may be used alone, blended with other bioabsorbable compositions, or in combination with non-bioabsorbable components. A wide variety of surgical articles may be manufactured from the polyurethanes, polyureas, polyamideurethanes, and/or polyureaurethanes described herein. These include but are not limited to clips and other fasteners, staples, sutures, pins, screws, prosthetic devices, wound dressings or coverings, burn dressings or coverings, drug delivery devices, anastomosis rings, stents, stent coatings, films, scaffolds, polyurethane foams, and other implantable medical devices. Examples of medical implantable devices include prosthetic devices, stents, sutures, staples, clips and other fasteners, screws, pins, films, meshes, drug delivery devices or systems, anastomosis rings, surgical dressings and the like. In some preferred embodiments, the surgical articles or components thereof include stents, stent coatings, wound coverings, burn coverings, foams, tissue engineering scaffolds, films, implantable medical devices, and/or controlled drug delivery systems, more preferably stents, stent coatings, wound and/or burn coverings, and/or controlled delivery systems. In certain other preferred embodiments, the surgical articles or components thereof include sutures, ligatures, needle and suture combinations, surgical clips, surgical staples, surgical prosthetic devices, textile structures, couplings, tubes, supports, screws, or pins. In certain preferred drug delivery systems, the systems comprise a polyurethane, polyurea, polyamideurethane, and/or polyureaurethane in admixture with a biologically or pharmaceutically active agent. Non-limiting examples of polymeric carriers in such drug delivery systems and/or pharmaceutical compositions include self-supporting films, hollow tubes, beads, and/or gels. Other preferred uses of the surgical article include their use as a scaffold for tissue engineering comprising a porous structure for the attachment and proliferation of cells. The polyurethanes, polyureas, polyamideurethanes, and/or polyureaurethanes herein may also be used to fabricate degradable containers and packaging materials which can degrade in landfills in contrast to existing non-degradable materials which present environmental concerns.

The polymers of the present invention may be used as pharmaceutical carriers in a drug delivery matrix. The matrix may be formed by mixing the polymer with a therapeutic agent. A vast variety of different therapeutic agents may be used in conjunction with the polymers of the invention. In general, therapeutic agents administered via the pharmaceutical compositions of the invention include, without limitation: anti-infectives such as antibiotics and antiviral agents; analgesics and analgesic combinations; anorexics; antihelmintics; antiarthritics; anti-asthmatic agents; anticonvulsants; antidepressants; antidiuretic agents; antidiarrheals; antihistamines; antiinflammatory agents; antimigraine preparations; antinauseants; antineo-plastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; para-sympatyholytics; psychostimulants; sedatives; and tranquilizers; and naturally derived or genetically engineered proteins, polysaccharides, glycoproteins or lipoproteins.

The drug delivery matrix may be administered in any suitable dosage form such as oral, parenteral, subcutaneously as an implant, vaginally or as a suppository. Matrix formulations containing polymers of the invention may be formulated by mixing one or more therapeutic agents with the polymer. The therapeutic agent may be present as a liquid, a finely divided solid, or any other appropriate physical form. Typically, the matrix will include one or more additives, e.g., nontoxic auxiliary substances such as diluents, carriers, excipients, stabilizers or the like. However, the presence of such additives is entirely optional. Other suitable additives may be formulated with the polymers of this invention and pharmaceutically active agent or compound. If water is to be used as an additive, it is preferably be added immediately before administration.

The amount of therapeutic agent will be dependent upon the particular drug employed and medical condition being treated. Typically, the amount of drug represents about 0.001% to about 70%, more typically about 0.01% to about 50%, and most typically about 0.1% to about 20% by weight of the matrix.

The quantity and type of polymer incorporated into a parenteral dosage form will vary depending on release profile desired and the amount of drug employed. The product may contain blends of polymers of this invention to provide the desired release profile or consistency to a given formulation.

The polymers of this invention, upon contact with body fluids including blood or the like, undergo gradual degradation (mainly through hydrolysis) with concomitant release of the dispersed drug for a sustained or extended period (as compared to the release from an isotonic saline solution). This may result in prolonged delivery (over about one to about 2,000 hours, preferably about two to about 800 hours) of effective amounts (including, for example, about 0.0001 mg/kg/hour to about 10 mg/kg/hour) of the drug. This dosage form may be administered as necessary depending on the subject being treated, the severity of the affliction, the judgment of the prescribing physician, and the like.

Individual formulations of drugs and polymers of this invention may be tested in appropriate in vitro and in vivo models to achieve the desired drug release profiles. For example, a drug may be formulated with a polymer of this invention and orally administered to an animal. The drug release profile may be monitored by appropriate means, such as by taking blood samples at specific times and assaying the samples for drug concentration. Following this or similar procedures, those skilled in the art may formulate a variety of formulations.

The polyurethane material is believed to be especially useful for use as a tissue engineering scaffold, i.e., as a structure for the growth or regeneration of tissue. Polyurethanes may lend themselves to such uses since the enzyme-catalyzed degradation may in some cases work concurrently with the migration or growth of cells into the material, while desirably degrading in the process into its substantially non-toxic constituents. It is also possible, in some cases, that cells migrating into or located adjacent the matrix may themselves exude proteolytic enzymes that will also mediate hydrolytic cleavage.

Such tissue engineering scaffolds may have applications in the regeneration of skin and other organs, bone, cartilage, ligaments, tendons, bladder and other tissue. The polyurethane material may also be useful in the production of sutures, which require good mechanical strength, and drug release matrices, in view of their need for non-toxic degradability. The polyurethane material may also be useful for other non-biomedical applications, where degradability into substantially non-toxic constituents is an asset. The polyurethane material lends itself to sterilization by such techniques as gamma radiation and ethylene oxide treatments.

Fibers made from the present polyurethanes, polyureas, polyamideurethanes, and/or polyureaurethanes can be knitted or woven with other fibers, either bioabsorbable or non-bioabsorbable to form meshes or fabrics. Compositions including these polyurethanes, polyureas, polyamideurethanes, and/or polyureaurethanes may also be used as an bioabsorbable coating for surgical devices.

In another aspect, the compositions containing the polyurethanes, polyureas, polyamideurethanes, and/or polyureaurethanes described herein may be used to make reinforced composites. Thus, for example, the polyurethane, polyurea, polyamideurethane, and/or polyureaurethane composition may form the matrix of the composite and may be reinforced with bioabsorbable or non-bioabsorbable fibers or particles. Alternatively, a matrix of any bioabsorbable or non-bioabsorbable polymer composition may be reinforced with fibers or particulate material made from compositions containing the polyurethanes, polyureas, polyamideurethanes, and/or polyureaurethanes described herein.

In an alternative embodiment, the polyurethanes, polyureas, polyamideurethanes, and/or polyureaurethanes described herein may be admixed with a filler. The filler may be in any particulate form, including granulate and staple fibers. While any known filler may be used, hydroxyapatite, tricalcium phosphate, bioglass or other bioceramics are the preferred fillers. Normally, from about 10 grams to about 400 grams of filler are mixed with about 100 grams of polymer. The filled, cross-linked polymers are useful, for example, as a molding composition.

It is further contemplated that one or more medico-surgically useful substances may be incorporated into compositions containing the polyurethanes, polyureas, polyamideurethanes, and/or polyureaurethanes described herein. Examples of such medico-surgically useful substances include, for example, those which accelerate or beneficially modify the healing process when particles are applied to a surgical repair site. For example, articles made from compositions containing the present polyurethanes, polyureas, polyamideurethanes, and/or polyureaurethanes may carry a therapeutic agent which will be deposited at the repair site. The therapeutic agent may be chosen for its antimicrobial properties, capability for promoting repair or reconstruction and/or new tissue growth. Antimicrobial agents such as broad spectrum antibiotic, for example, gentamycin sulfate, erythromycin, or derivatized glycopeptides which are slowly released into the tissue may be applied in this manner to aid in combating clinical and sub-clinical infections in a tissue repair site. To promote repair and/or tissue growth, one or several growth promoting factors may be introduced into the articles, e.g., fibroblast growth factor, bone growth factor, epidermal growth factor, platelet derived growth factor, macrophage derived growth factor, alveolar derived growth factor, monocyte derived growth factor, magainin, and the like. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is contemplated that it may be desirable to dye articles made from compositions containing the present polyurethanes, polyureas, polyamideurethanes, and/or polyureaurethanes in order to increase visibility of the article in the surgical field. Dyes, such as those known to be suitable for incorporation in sutures, may be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979), the disclosures of which are hereby incorporated herein by reference, in their entireties. Preferably, articles in accordance with this disclosure may be dyed by adding up to about a few percent and preferably about 0.2% dye to the resin composition prior to extrusion.

The compounds employed in the methods of the present invention may be prepared in a number of ways well known to those skilled in the art. The compounds may be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

The following examples are included to further illustrate the invention and are not to be considered as limiting the invention anyway. Melting points were measured for all products by using a Polmon (MP 96) melting point apparatus. For all the products, NMR was run using a Varian 200 MHz and tetramethylsilane as an internal standard.

EXAMPLES

Example 1

Chloro-Acetic Acid 2-(2-chloro-acetoxy)-ethyl Ester (1)

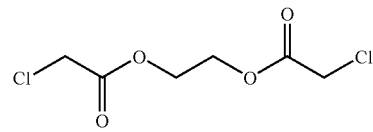 [SMILES: O=C(CCl)OCCOC(=O)CCl]

In a 2 liter, 4 necked round bottom flask equipped with a mechanical stirrer, a solution of ethylene glycol (100 grams, 1.611 moles), chloroacetic acid (385 grams, 4.031 moles) and para toluenesulphonic acid (1 gram) in toluene (750 ml), was refluxed for 8 hours using a Dean-Stark apparatus. It was then cooled to room temperature. The toluene layer was washed with water (2×300 ml), 5% sodium bicarbonate solution (3×500 ml) and again with water (2×300 ml), dried over sodium sulfate, and distilled to provide crude 1, which was purified by high vacuum distillation to provide pure 1 (242 grams, 69.8%), which slowly crystallized to white crystals. m.p: 44° C., $^1$H NMR (CDCl$_3$) δ 4.16 (s, 2H, CH$_2$), 4.85 (s, 2H, CH$_2$)

Example 2

(4-Nitro-phenoxy)-acetic acid-2-[2-(4-nitro-phenoxy)-acetoxy]-ethyl Ester (2)

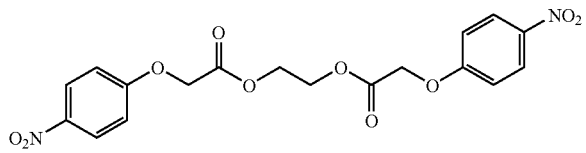 [SMILES: O=C(COc1ccc([N+](=O)[O-])cc1)OCCOC(=O)COc1ccc([N+](=O)[O-])cc1]

To a stirred solution of 4-nitrobenzoic acid (583 grams) in 1.2 liters of dry dimethylformamide (DMF) was added 583 ml of triethylamine followed by 300 grams of 1. The solution was placed in an oil bath maintained at 50° C. for about 20 hours. The progress of the reaction was monitored from time to time using TLC to monitor the disappearance of starting materials. The reaction mixture was precipitated in cold water. The solid precipitate was taken into 5% NaHCO₃ solution, followed by filtration and then again washed with water to obtain 2 kilograms of crude 2. Crude 2 was purified by crystallization using 1:1 solution of methanol:chloroform to obtain 476 grams of purified product 2 as an off-white powder with a melting point of 118-121° C.

Example 3

(4-Amino-phenoxy)-acetic acid-2-[2-(4-amino-phenoxy)-acetoxy]-ethyl Ester (3)

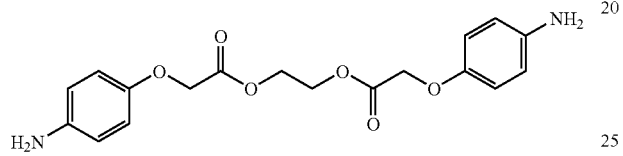

Compound 2 (100 grams) was dissolved in 200 ml of dry dimethylformamide (DMF) in a pressure vessel followed by addition of 30 grams of Raney Nickel catalyst. The mixture was stirred under an atmosphere of hydrogen for about 10 hours. The disappearance of the starting material using TLC confirmed the completion of reaction. The catalyst was removed by filtration. About 80% of the DMF was distilled off under high vacuum. The compound was precipitated from the residual solution by addition to methanol to give 75 grams of pure 3 as an off-white powder. m.p: 182-185° C.

Example 4

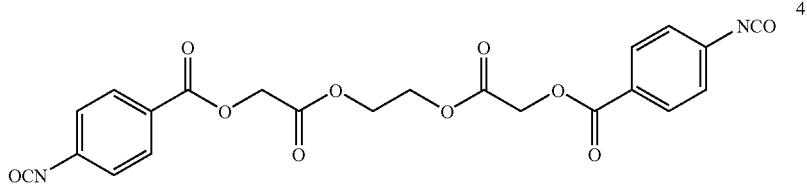

In a 1 liter round bottom flask, 150 grams of 3 was dissolved in 4.5 liters of 1,4-dioxane (500 ml) followed by sparging with nitrogen into the solution to remove dissolved oxygen. The flask was placed in an oil bath maintained at 100° C. followed by a dropwise addition of a solution of 321 grams of triphosgene in 600 ml of 1,4-dioxane to the flask. After 16 hours, 40 grams of triphosgene was further added to the solution. The reflux condenser was replaced with a distillation set up. 1,4-Dioxane was distilled off under vacuum followed by release of vacuum using a nitrogen bleed. 2.5 Liters of fresh 1,4-dioxane was further added followed by distillation under vacuum. The vacuum was released using a nitrogen bleed. This was followed by addition of 3.75 liters of toluene to the reaction mixture along with 25 grams of activated carbon. The hot toluene solution was filtered to remove activated carbon. The residual toluene solution was cooled and filtered. Distillation of the toluene provided 106 grams of pure 4 as a white powder. m.p: 138-141° C.

Example 5

6-Bromo-Hexanoic Acid 2-(6-bromo-hexanoyloxy)-ethyl Ester

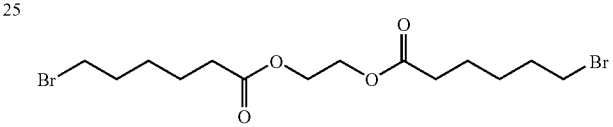

In a 1 liter, 4 neck round bottom flask equipped with a mechanical stirrer, a solution of 5 grams of ethylene glycol, 47 grams of 6-bromo hexanoic acid and 0.5 gram of para-toluenesulphonic acid in 150 ml of toluene was refluxed for 4 hours using a Dean-Stark apparatus. The solution was cooled to room temperature. The toluene layer was washed with water (2×100 ml), 5% sodium bicarbonate solution (3×50 ml), water (2×100 ml), dried over sodium sulfate, and distilled to get 30 grams of 5 as light yellow syrup. m.p: 44° C., ¹H NMR (CDCl₃) δ 1.45 (m, 2H, CH₂), 1.59 (m, 2H, CH₂), 1.82 (m, 2H, CH₂), 2.26 (t, 2H, CH₂), 3.34 (t, 2H, CH₂), 4.18 (s, 2H, CH₂)

Example 6

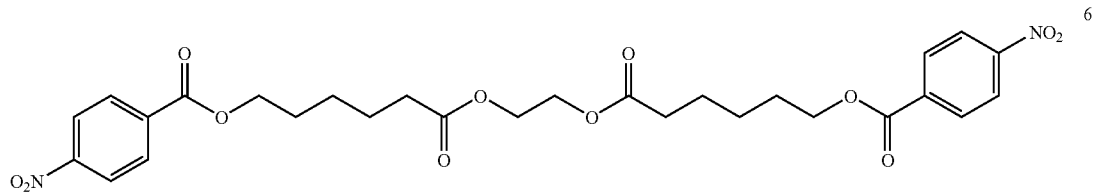 [SMILES: O=C(CCCCCOC(=O)c1ccc([N+](=O)[O-])cc1)OCCOC(=O)CCCCCOC(=O)c1ccc([N+](=O)[O-])cc1]

To a solution of 12 grams of 4-nitrobenzoic acid and 11 grams of triethylamine in 25 ml dimethylformamide was added dropwise 10 grams of 5 and the mixture was stirred at room temperature for 16 hours. The solids were filtered off, the dimethylformamide solution was added onto 5% sodium bicarbonate solution (1 liter) and crude 6 was extracted into chloroform, dried over sodium sulfate, distilled, and purified by column chromatography on silica gel using toluene as eluent to get 9 grams of pure 6 as a light cream powder. m.p: 71-73° C., $^1$H NMR (CDCl$_3$) δ 1.50 (m, 2H, CH$_2$), 1.80 (m, 4H, CH$_2$), 2.36 (t, 2H, CH$_2$), 4.26 (s 2H, CH$_2$), 4.34 (t, 2H, CH$_2$), 8.28 (dd, 4H, Ar)

Example 7

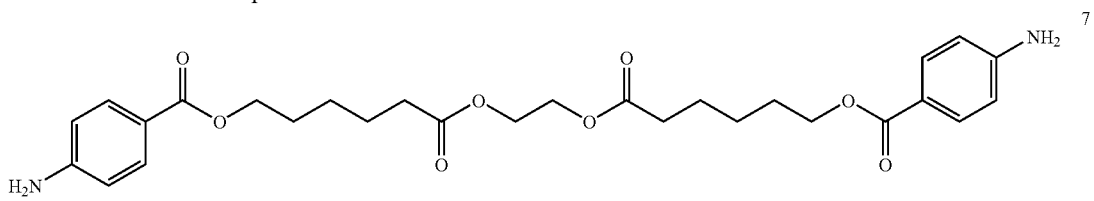

Compound 6 (25 grams) was dissolved in 200 ml of dimethylformamide (DMF) in a pressure vessel, 15 grams of Raney-Nickel catalyst were added, and the mixture was stirred under an atmosphere of hydrogen for 24 hours. The catalyst was removed by filtration, DMF distilled under vacuum and crude 7 was purified by column chromatography using chloroform: ethyl acetate (9:1) as eluent to get 15 grams of pure 7 as a light brown powder. m.p: 70-73° C., $^1$H NMR (CDCl$_3$) δ 1.46 (m, 2H, CH$_2$), 1.70 (m, 4H, CH$_2$), 2.32 (t, 2H, CH$_2$), 4.14 (bs, 2H, NH$_2$), 4.20 (s &t, 4H, CH$_2$), 6.56 (d, 2H, Ar), 7.80 (d, 2H, Ar). In vitro hydrolysis of 50 mg of 7 in 50 ml, pH 9 buffer at 100° C., resulted in complete hydrolysis in about 15 hours.

Example 8

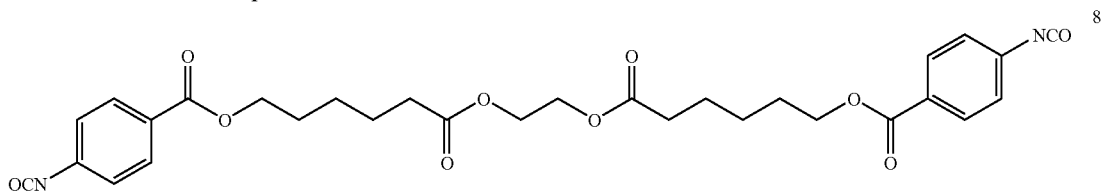

Compound 8 was prepared starting from 7 using the same procedure as described in Example 4.

Example 9

Chloroacetic Acid 3-(2-chloro-acetoxy)-propyl Ester

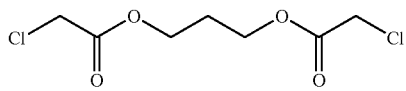

In a 1 liter, 4 neck round bottom flask equipped with a mechanical stirrer, a solution of 25 grams of 1,3-propanediol, 94 grams of chloroacetic acid and 1 gram of para-toluenesulphonic acid in 250 ml of toluene was refluxed for 8 hours using a Dean-Stark apparatus. The solution was cooled to room temperature. The toluene layer was washed with water (2×300 ml), 5% sodium bicarbonate solution (3×300 ml), water (2×300 ml), dried over sodium sulfate, and distilled to get crude 9, which was purified by high vacuum distillation to get 72 grams of pure 9 as a colorless liquid. $^1$H NMR (CDCl$_3$) δ 2.10 (m, 2H, CH$_2$), 4.08 (s, 4H, CH$_2$), 4.30 (t, 4H, CH$_2$).

Example 10

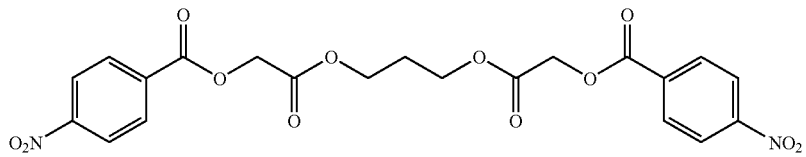

To a solution of 32.8 grams of 4-nitrobenzoic acid and 30 grams of triethylamine in 40 ml of dimethylformamide was added 15 grams of 9 in small portions and the mixture was stirred at room temperature for 6 hours. The solids were filtered off, the dimethylformamide solution was added onto 5% sodium bicarbonate solution (150 ml), filtered crude 10, recrystallised in chloroform:methanol (1:1) to get 9 grams of pure 10 as a light cream powder. m.p: 120-121.8° C., $^1$H NMR (CDCl$_3$) δ 2.08 (m, 1H, CH), 4.30 (t, 2H, CH$_2$), 4.88 (s, 2H, CH$_2$), 8.30 (dd, 4H, Ar)

Example 11

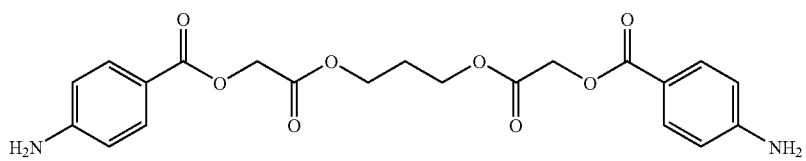

Compound 10 (5 grams) was dissolved in 100 ml dimethylformamide and 100 ml methanol in a pressure vessel, 3 grams of Raney-Nickel catalyst was added and the mixture was stirred under an hydrogen atmosphere for 24 hours. The catalyst was removed by filtration, solvent distilled under vacuum followed by addition of 20 ml of ice water, filtered crude 11 which was recrystallised from a mixture of dimethylformamide:methanol (1:7) to get pure 11 (3 grams, 68.49%) as a light brown powder. m.p: 130.3-132.4° C., $^1$H NMR (DMSO-d$_6$) δ 2.00 (m, 1H, CH$_2$), 4.22 (t, 2H, CH$_2$), 4.74 (s, 2H, CH$_2$), 5.36 (bs, 2H, NH2), 6.60 (d, 2H, Ar), 7.74 (d, 2H, Ar). In vitro hydrolysis of 50 mg of 11 in 50 ml, pH 9 buffer at 100° C., resulted in complete hydrolysis in about 29 hours.

Example 12

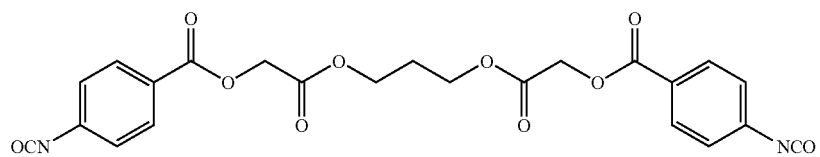

Compound 12 was prepared starting from 11 using the same procedure as described in Example 4.

Example 13

Chloroacetic Acid 3-(2-chloroacetoxy)-2,2-bis-(2-chloroacetoxymethyl)-propyl Ester

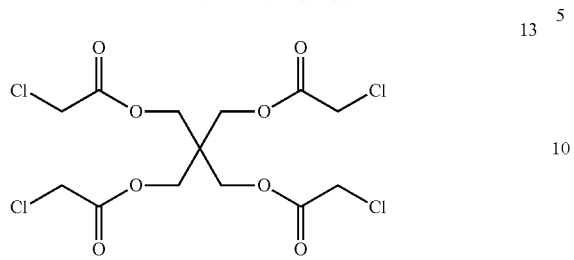

In a 2 liter, 4 neck round bottom flask equipped with a mechanical stirrer, a solution of 25 grams of pentaerythritol, 105.2 grams of chloroacetic acid and 2 grams of para toluenesulphonic acid in 500 ml toluene was refluxed for 8 hours using Dean-Stark apparatus. The solution was cooled to room temperature. The toluene layer was washed with water (2×300 ml), 5% sodium bicarbonate solution (3×500 ml), water (2×300 ml), dried over sodium sulfate, and distilled to get crude 13, which was purified by recrystallization from chloroform:hexane (1:7) to get pure 13 (77 grams, 94.8%), as white powder. m.p: 94-96° C., $^1$H NMR (CDCl$_3$) δ 4.16 (s, 2H, CH$_2$), 4.28 (s, 2H, CH$_2$)

Example 14

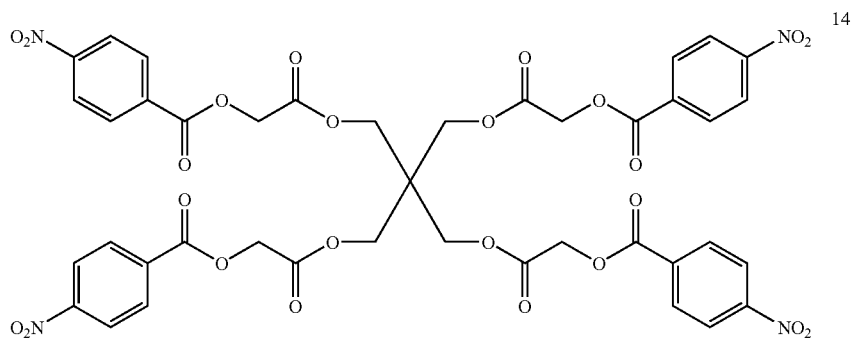 [SMILES: O=C(COC(=O)c1ccc([N+](=O)[O-])cc1)OCC(COC(=O)COC(=O)c1ccc([N+](=O)[O-])cc1)(COC(=O)COC(=O)c1ccc([N+](=O)[O-])cc1)COC(=O)COC(=O)c1ccc([N+](=O)[O-])cc1]

To a solution of 11.3 grams of 4-nitrobenzoic acid, 9.2 grams of triethylamine in 25 ml of dimethylformamide was added 5 grams of 13 in small portions and stirred at room temperature for 5 hours. The solids were filtered off; the dimethylformamide solution was added onto 1 liter of 5% sodium bicarbonate solution followed by filtration and washing with methanol. The solution was dried to obtain 9 grams of 14 as an off-white powder. An analytical sample was prepared by column chromatography on silica gel using chloroform as eluent. m.p: 117-121° C., $^1$H NMR (CDCl$_3$) δ 4.14 (s, 2H, CH$_2$), 4.84 (s, 2H, CH$_2$), 8.25 (dd, 4H, Ar)

Example 15

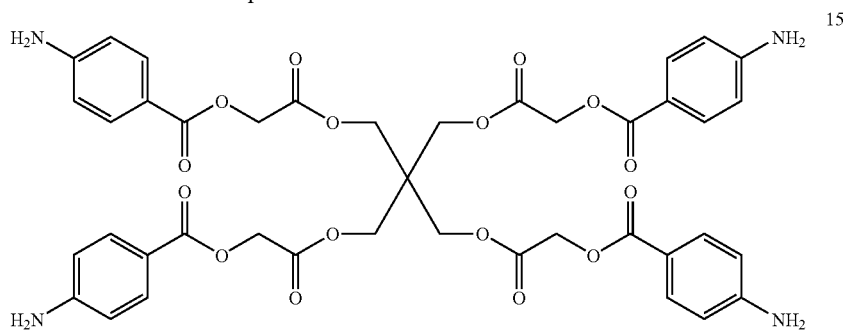

Compound 14 (25 grams) was dissolved in 100 ml of dimethylformamide in a pressure vessel, 10 grams of Raney-Nickel catalyst were added, and the mixture was stirred under an hydrogen atmosphere for 5 hours. The catalyst was removed by filtration, and crude 15 was precipitated by adding methanol, filtered, and dried to get 20 grams of pure 15 as a white fluffy powder. m.p: 192-194.4° C., $^1$H NMR (DMSO-$d_6$), δ 4.25 (s, 2H, $CH_2$), 4.81 (s, 2H, $CH_2$), 6.09 (bs, 2H, $NH_2$), 6.55 (d, 2H, Ar), 7.67 (d, 2H, Ar). In vitro hydrolysis of 50 mg of 15 in 50 ml, pH 9 buffer at 100° C., resulted in complete hydrolysis in about 6 hours.

Example 16

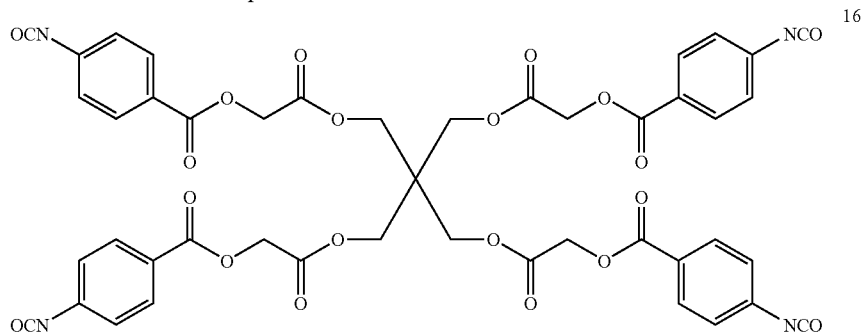

Compound 16 was prepared starting from 15 using the same procedure as described in Example 4.

Example 17

Chloroacetic Acid 2,3-bis-(2-chloroacetoxy)-propyl Ester

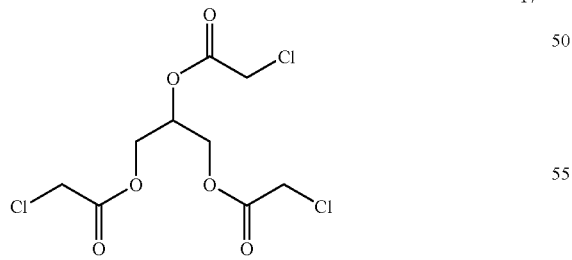

In a 2 liter, 4 neck round bottom flask equipped with a mechanical stirrer, a solution of 25 grams of glycerol, 116 grams of chloroacetic acid and 2 grams of para toluenesulphonic acid in 500 ml of toluene (500 ml) was refluxed for 6 hours using a Dean-Stark apparatus. The solution was then cooled to room temperature. The toluene layer was washed with water (2×300 ml), 5% sodium bicarbonate solution (3×500 ml), water (2×300 ml), dried over sodium sulfate, and distilled to get 67 grams of crude 17 as a colorless liquid.

Example 18

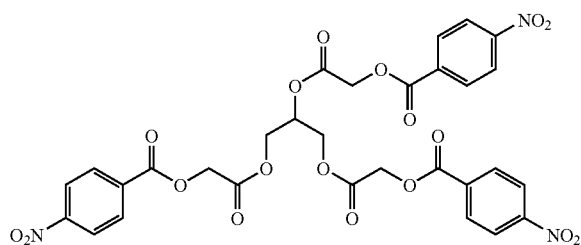

To a solution of 23.4 grams 4-nitrobenzoic acid and 18.9 grams of triethylamine in dimethylformamide (30 ml) was added 10 grams of 17 in small portions and stirred at room temperature for 16 hours. The solids were filtered off, the dimethylformamide solution was added onto 5% sodium bicarbonate solution (500 ml), extracted into chloroform, washed with water (2×50 ml), dried over sodium sulfate, and distilled to get crude 18, which was purified by column chromatography on silica gel using toluene as eluent to get 6 grams of pure 18 as a light yellow syrup. $^1$H NMR (DMSO-$d_6$) δ 4.42 (m, 4H, $CH_2$), 4.92 (Over lapped s, 6H, $CH_2$), 5.42 (m, 1H, CH), 8.28 (over lapped d, 12H, Ar)

Example 19

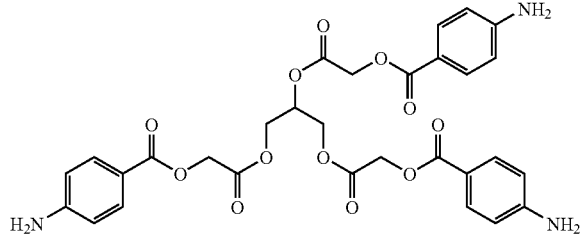

Compound 18 (10 grams) was dissolved in 150 ml dimethylformamide in a pressure vessel, 15 grams of Raney-Nickel catalyst was added and the mixture was stirred under an atmosphere of hydrogen for 16 hours. The catalyst was removed by filtration, the filtrate was poured on to ice water (300 ml), extracted with ethyl acetate followed by drying over sodium sulfate. The dried solution was treated with activated charcoal, the charcoal was filtered off, and the solvent was distilled off under vacuum to get 6 grams of pure 19 (68.7%) as a light yellow syrup. $^1$H NMR ($CDCl_3$+DMSO-$d_6$), δ 4.35 (m, 4H, $CH_2$), 4.78 (over lapped s, 6H, $CH_2$), 5.30 (m, 1H, CH), 6.62 (d, 2H, Ar), 7.70 (d, 2H, Ar). In vitro hydrolysis of 50 mg of 19 in 50 ml, pH 9 buffer at 100° C., resulted in complete hydrolysis in about 10 hours.

Example 20

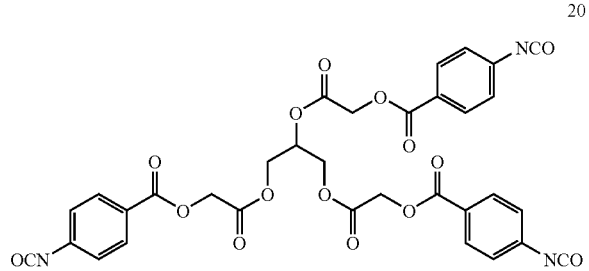

Compound 20 was prepared starting from 19 using the same procedure as described in Example 4.

Example 21

Chloroacetic Acid 4-(2-chloroacetoxy)-butyl Ester

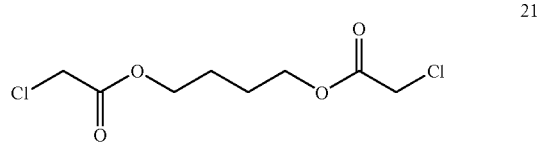 [SMILES: O=C(CCl)OCCCCOC(=O)CCl]

In a 2 liter, 4 neck round bottom flask equipped with a mechanical stirrer, a solution of 75 grams of 1,4-butanediol, 240 grams of chloroacetic acid and 3 grams of para-toluenesulphonic acid 750 ml toluene was refluxed for 6 hours using a Dean-Stark apparatus. The solution was then cooled to room temperature. The toluene layer was washed with water (2×300 ml), 5% sodium bicarbonate solution (3×500 ml), water (2×300 ml), dried over sodium sulfate, and distilled to get crude 21, which was purified by recrystallization in chloroform:hexane (1:7) to get 92 grams of pure 21 as a white fluffy powder. m.p: 74-76.5° C., $^1$H NMR ($CDCl_3$) δ 1.78 (t, 2H, $CH_2$), 4.05 (s, 2H, $CH_2$), 4.25 (t, 2H, $CH_2$)

Example 22

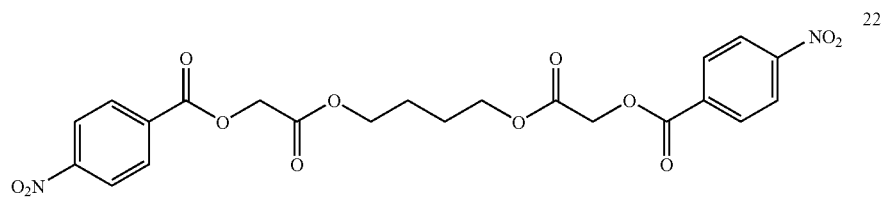 [SMILES: O=C(COC(=O)c1ccc([N+](=O)[O-])cc1)OCCCCOC(=O)COC(=O)c1ccc([N+](=O)[O-])cc1]

To a solution of 10.3 grams of 4-nitrobenzoic acid and 10.4 grams of triethylamine in 25 ml of dimethylformamide, 5 grams of 21 was added in small portions and stirred at room temperature for 16 hours. The solids were filtered off, the dimethylformamide solution was added onto 5% sodium bicarbonate solution (250 ml) followed by filtration to obtain crude 22 which was recrystallized in a mixture of chloroform: hexane (1:7) to get 4.8 grams of pure 22 as a white powder. m.p: 122.5-125° C., $^1$H NMR (CDCl$_3$) δ 1.78 (t, 2H, CH$_2$), 4.24 (t, 2H, CH$_2$), 4.86 (s, 2H, CH$_2$) 8.32 (dd, 4H, Ar)

Example 23

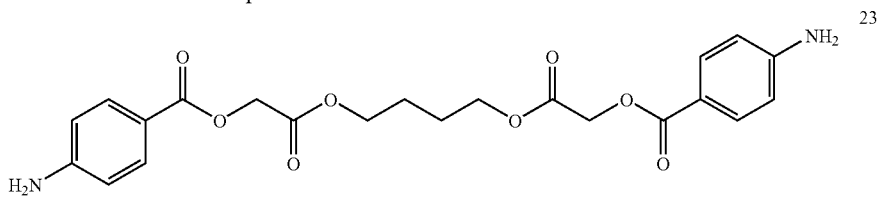

Compound 22 (25 grams) was dissolved in dimethylformamide (200 ml) in a pressure vessel, 15 grams of Raney-Nickel catalyst was added and the mixture stirred under hydrogen atmosphere for 18 hours. The catalyst was removed by filtration and to the filtrate was added ice water (500 ml), the precipitated product was filtered, dried and washed with hot ethyl acetate to get 14 grams of pure 23 as a white powder. m.p: 192.7-195.4, $^1$H NMR (DMSO-d$_6$) δ 1.75 (t, 2H, CH$_2$), 4.17 (t, 2H, CH$_2$), 4.85 (s, 2H, CH$_2$), 6.15 (s, 2H, NH2), 6.67 (d, 2H, Ar), 7.80 (d, 2H, Ar). In vitro hydrolysis of 50 mg of 23 in 50 ml, pH 9 buffer at 100° C., resulted in complete hydrolysis in about 24 hours.

Example 24

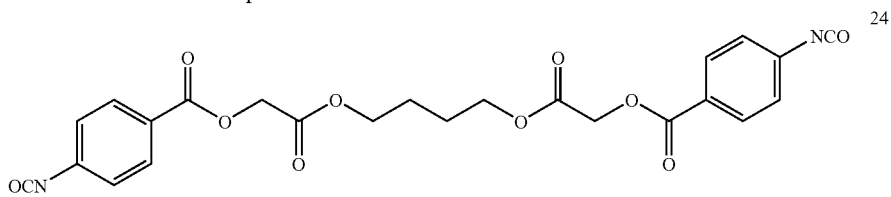

Compound 24 was prepared starting from 23 using the same procedure as described in Example 4.

Example 25

Chloroacetic Acid 2-[2-(2-chloroacetoxy)-ethoxy]-ethyl Ester

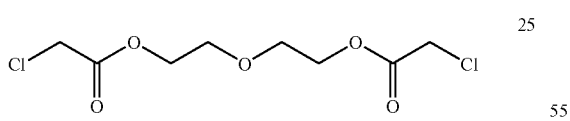

In a 2 liter, 4 neck round bottom flask equipped with a mechanical stirrer, a solution of 25 grams of diethylene glycol, 66 grams of chloroacetic acid and 1 gram of para-toluenesulphonic acid in 350 ml of toluene was refluxed for 6 hours using a Dean-Stark apparatus. The solution was cooled to room temperature. The toluene layer was washed with water (2×300 ml), 5% sodium bicarbonate solution (3×500 ml), water (2×300 ml), dried over sodium sulfate, and distilled to get 56 grams of 25 as a light yellow syrup. $^1$H NMR (CDCl$_3$) δ 3.75 (t, 2H, CH$_2$), 4.12 (s, 2H, CH$_2$), 4.36 (t, 2H, CH$_2$).

Example 26

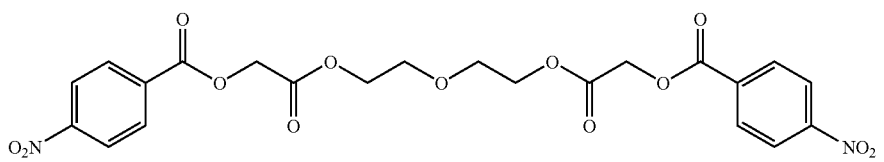

To a solution of 29 grams of 4-nitrobenzoic acid and 29 grams of triethylamine in 75 ml of dimethylformamide was added dropwise 15 grams of 25 and the mixture was stirred at room temperature for 18 hours. The solids were filtered off, the residual dimethylformamide solution was added into ice water (300 ml), extracted with chloroform, washed with 5% sodium bicarbonate solution (3×50 ml), water (100 ml), dried over sodium sulfate, and distilled to get crude 26 which was purified by column chromatography on silica gel using benzene as eluent to get pure 26 (10 grams, 33.22%) as light cream powder. m.p: 62-64° C., $^1$H NMR (CDCl$_3$) δ 3.72 (t, 2H, CH$_2$), 4.34 (t, 2H, CH$_2$), 4.92 (s, 2H, CH$_2$), 8.30 (over lapped d, 4H, Ar)

Example 27

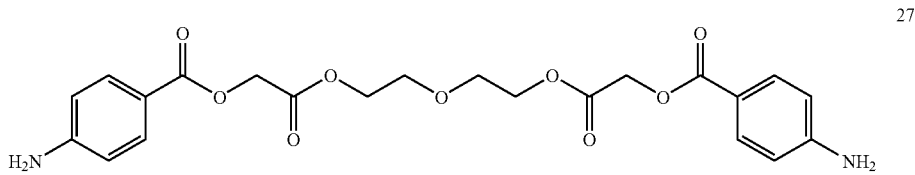 [SMILES: O=C(COC(=O)c1ccc([N+](=O)[O-])cc1)OCCOCCOC(=O)COC(=O)c1ccc([N+](=O)[O-])cc1]

Compound 26 (80 grams, 173.91 mmoles) was dissolved in dimethylformamide (300 ml) in a pressure vessel, Raney-Nickel (40 grams) was added and the mixture was stirred under an atmosphere of hydrogen (4 Kg) for 16 hours. The catalyst was removed by filtration and to the filtrate was added ice water (700 ml), the mixture was filtered, dried and washed with hot methanol to get pure 27 (56.6 grams, 80%) as a white powder. m.p: 136-137° C., $^1$H NMR (CDCl$_3$+DMSO-d$_6$) δ 3.62 (t, 2H, CH$_2$), 4.20 (t, 2H, CH$_2$), 4.81 (s, 2H, CH$_2$), 6.08 (s, 2H, NH$_2$), 6.58 (d, 2H, Ar), 7.78 (d, 2H, Ar). In vitro hydrolysis of 50 mg of 27 in 50 ml, pH 9 buffer at 100° C., resulted in complete hydrolysis in about three hours.

Example 28

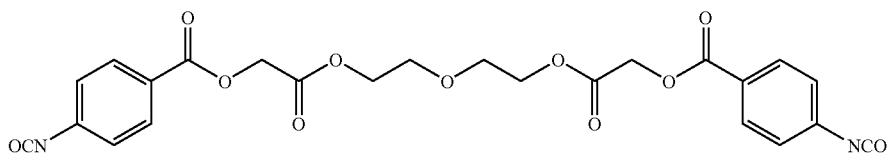

Compound 28 was prepared starting from 27 using the same procedure as described in Example 4.

Example 29

General Scheme for Synthesis of Polyurethane Polymer (Para Isomer Shown) from Isocyanates of General Formula I Given Below

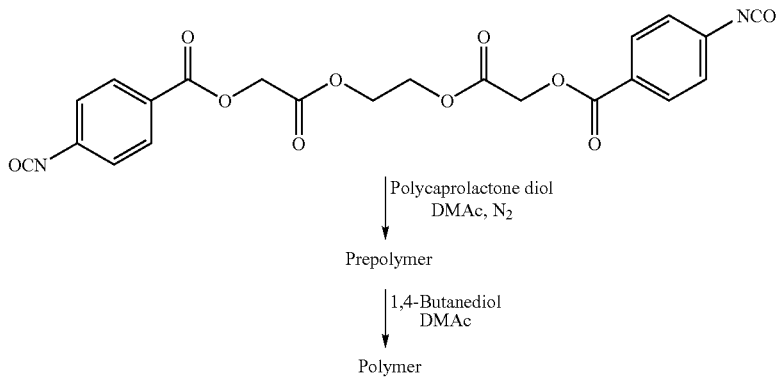

Example 30

Synthesis of Polyurethane Via Solution Polymerization and Physical Properties

In accordance with the general scheme depicted in Example 29 for synthesis of polyurethane polymer from isocyanates of general Formula I, polyurethane was prepared via solution polymerization the following manner. Into a clean and dry 1 liter, 4-necked round bottomed flask equipped with a desiccant tube and maintained under nitrogen atmosphere was added 8.3 grams of dibenzoic acid based diisocyanate from example 4 and 25 ml of dimethylacetamide. The flask was placed in an oil bath maintained at 50° C. and stirred on a magnetic stirrer until a clear solution was obtained. To this stirring solution of diioscyanate and dimethylacetamide was added 10 grams of polycaprolactone diol. The temperature of the oil bath was increased to 60° C. and the reaction mixture was left stirring for 1.5 hours. To this stirring solution was added 0.9 grams of 1,4-butanediol dissolved in 5 ml of dimethylacetamide and one drop of stannous octanoate catalyst. The reaction mixture was left stirring at 60° C. for another hour and then a small portion of the polyurethane solution was poured onto a Gardner coater to prepare a film. GPC analysis of the polyurethane film revealed a weight average molecular weight of 81,925 and a polydispersity index of 1.5. The maximum tensile strength and percent elongation range of the polyurethane films prepared using the Gardner coater was determined to be 278 psi and 943% elongation respectively using an Instron tensile tester.

Example 31

Synthesis of Polyurethane Via Melt Polymerization

In accordance with the general scheme depicted in Example 29 for synthesis of polyurethane polymer from isocyanates of general Formula I, polyurethane was prepared via melt polymerization in the following manner. Into a clean and dry 1 liter, 4-necked round bottomed flask equipped with a desiccant tube and maintained under nitrogen atmosphere was added 8.3 grams of dibenzoic acid based diisocyanate from Example 4 and 10 grams of polycaprolactone diol at room temperature. The flask was placed in an oil bath maintained at 70° C. and placed on a magnetic stirrer. The temperature of the oil bath was slowly increased from 70 to 90 and finally to 140° C. over approximately one hour by which time the mixture had melted. To this stirring solution was added 0.9 grams of 1,4-butanediol and one drop of stannous octanoate catalyst. The reaction mixture was left stirring at 140° C. for another hour and a solid polyurethane was obtained. GPC analysis of the polyurethane revealed a weight average molecular weight of 89,000 and a polydispersity index of 1.5.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A surgical article or component thereof comprising a polyurethane, polyurea, polyamideurethane or polyureaurethane, formed by polymerizing a biocompatible and bioabsorbable polyisocyanate of Formula I:

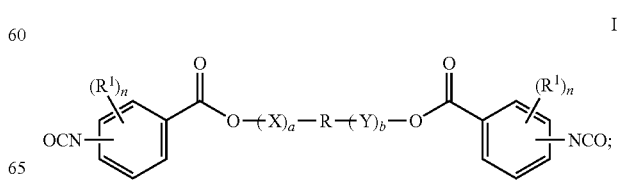

with a compound selected from a polyol, an amine, and an amide-diol;
wherein:
R is alkylene-$[C(R^4)(R^5)]_s$-alkylene-, wherein:
(1) one or more of the —$CH_2$— moieties in one or more alkylene chain portions of R are optionally replaced by —O— or —S—; or
(2) one or more of the —$CH_2$—$CH_2$— moieties in the alkylene chain portions of R are optionally replaced by —C(=O)—O— or —O—C(=O)—;
each $R^1$ is independently $[—C(R^2)(R^3)—]_p$-Z;
each Z is independently alkoxy, aralkyloxy, —C(=O)—H, halogen, —C(=O)—OH, or —$NO_2$;
each $R^2$ and $R^3$ is independently H or alkyl;
$R^4$ is H, $OR^6$ or $CH_2OR^6$;
$R^5$ is H or $CH_2OR^6$;
each $R^6$ is independently:

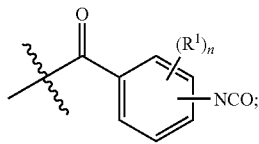

each X is —$(CH_2CH_2O)_z$—$CH_2$—C(=O)—O—;
each Y is —O—C(=O)—$CH_2$—$(OCH_2CH_2)_z$—;
each a and b is independently an integer from about 1 to about 6;
n is an integer from about 0 to about 4;
p is an integer from about 0 to about 10;
s is the integer 0 or 1; and
each z is 1.

2. A surgical article according to claim 1, wherein the polyisocyanate of Formula I has the following Formula Ia:

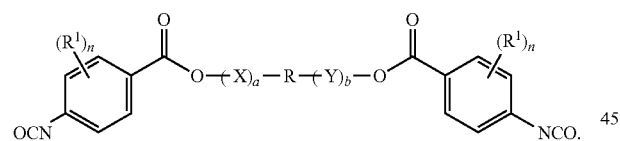

3. A surgical article according to claim 1, wherein s is 0.

4. A surgical article or component thereof according to claim 1, which is a stent, stent coating, wound covering, burn covering, foam, tissue engineering scaffold, film, implantable medical device, or controlled drug delivery system.

5. A surgical article or component thereof according to claim 1, which is a suture, ligature, needle and suture combination, surgical clip, surgical staple, surgical prosthesis, textile structure, coupling, tube, support, screw, or pin.

6. A surgical article or component thereof according to claim 4, which is a stent.

7. A surgical article or component thereof according to claim 4, which is a stent coating.

8. A surgical article or component thereof according to claim 4, which is a controlled delivery system.

9. A surgical article or component thereof according to claim 8, wherein a biologically or a pharmacologically active agent is physically embedded or dispersed into the polyurethane, polyurea, polyamideurethane, or polyureaurethane polymer matrix of the controlled delivery system.

10. A surgical article or component thereof according to claim 4, which is a tissue engineering scaffold having a porous structure for the attachment and proliferation of cells in vitro or in vivo.

11. A surgical article or component thereof according to claim 4, which is a wound or burn covering.

12. A surgical article or component thereof according to claim 11, which is at least partially biodegradable.

13. A surgical article of claim 1, wherein the polyurethane, polyurea, polyamideurethane or polyureaurethane is further polymerized with a lactone monomer selected from glycolide, lactide, .epsilon.-caprolactone, trimethylene carbonate, and p-dioxanone.

14. A surgical article or component thereof comprising a polyurethane, polyurea, polyamideurethane or polyureaurethane, formed by polymerizing a biocompatible and bioabsorbable polyisocyanate of Formula I:

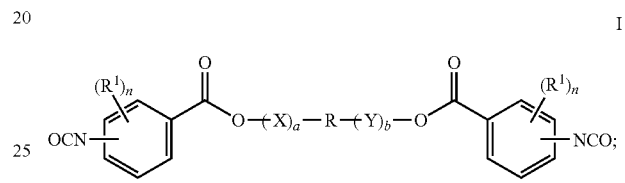

with a compound selected from a polyol, an amine, and an amide-diol;
wherein:
R is alkylene-$[C(R^4)(R^5)]_s$-alkylene-, wherein:
(1) one or more of the —$CH_2$— moieties in one or more alkylene chain portions of R are optionally replaced by —O— or —S—; or
(2) one or more of the —$CH_2$—$CH_2$— moieties in the alkylene chain portions of R are optionally replaced by —C(=O)—O— or —O—C(=O)—;
each $R^1$ is independently $[—C(R^2)(R^3)—]_p$-Z;
each Z is independently alkoxy, aralkyloxy, —C(=O)—H, halogen, —C(=O)—OH, or —$NO_2$;
each $R^2$ and $R^3$ is independently H or alkyl;
$R^4$ is H, alkyl, $(Y^1)_cOR^6$, $OR^6$, $CH_2$—$(Y^2)_dOR^6$, or $CH_2OR^6$;
$R^5$ is H, alkyl, $CH_2$—$(Y^2)_dOR^6$, or $CH_2OR^6$;
each $R^6$ is independently:

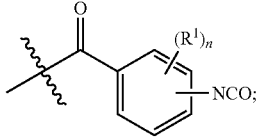

each X is —$(CH_2CH_2O)_z$—$CH_2$—C(=O)—O—;
each Y, $Y^1$, and $Y^2$ is independently —O—C(=O)—$CH_2$—$(OCH_2CH_2)_z$—;
each a, b, c, and d is independently an integer from about 1 to about 6;
n is an integer from about 0 to about 4;
p is an integer from about 0 to about 10;
s is the integer 0 or 1; and
each z is 1.

15. A surgical article or component thereof of claim 14, wherein $R^4$ is H.

16. A surgical article or component thereof of claim 15, wherein $R^5$ is H.

17. A surgical article or component thereof of claim 14, wherein $R^4$ is alkyl.

18. A surgical article or component thereof of claim 17, wherein $R^5$ is $CH_2$—$(Y^2)_d OR^6$.

19. A surgical article or component thereof of claim 14, wherein $R^4$ is $CH_2$—$(Y^2)_d OR^6$.

20. A surgical article or component thereof of claim 19, wherein $R^5$ is $CH_2$—(Y2)$_d$OR6.

21. A surgical article or component thereof of claim 18 wherein d is 1.

22. The surgical article of claim 1, wherein the article is a polyurethane is formed by polymerizing a biocompatible and bioabsorbable polyisocyanate of Formula I with a polyol selected from:
 a) 1,2-ethanediol (ethylene glycol);
 b) 1,2-propanediol (propylene glycol);
 c) 1,3-propanediol;
 d) 1,4-butanediol;
 e) 1,5-pentanediol;
 f) 1,3-cyclopentanediol;
 g) 1,6-hexanediol;
 h) 1,8-octanediol;
 i) a polyethylene glycol with a molecular weight from about 500 to about 10000;
 j) polytetramethylene ether glycol; and,
 k) a polyol with a molecular weight of about 500 to about 10000 derived from a compound selected from glycolide, lactide, trimethylenecarbonate, p-dioxanone, caprolactone, and combinations thereof.

23. The surgical article of claim 1, wherein the article is a polyurea formed by polymerizing a biocompatible and bioabsorbable polyisocyanate of Formula I with an amine selected from:

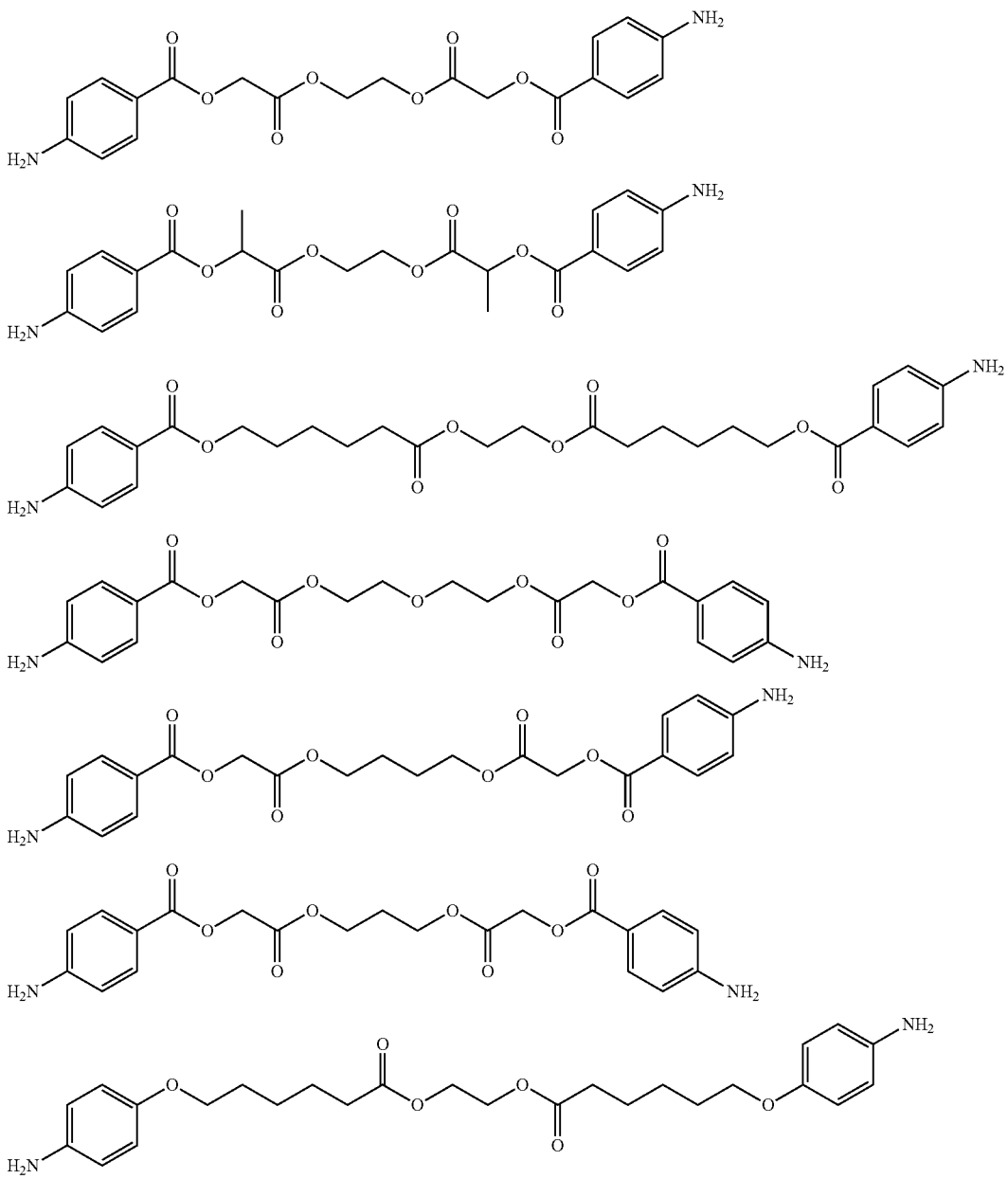

-continued
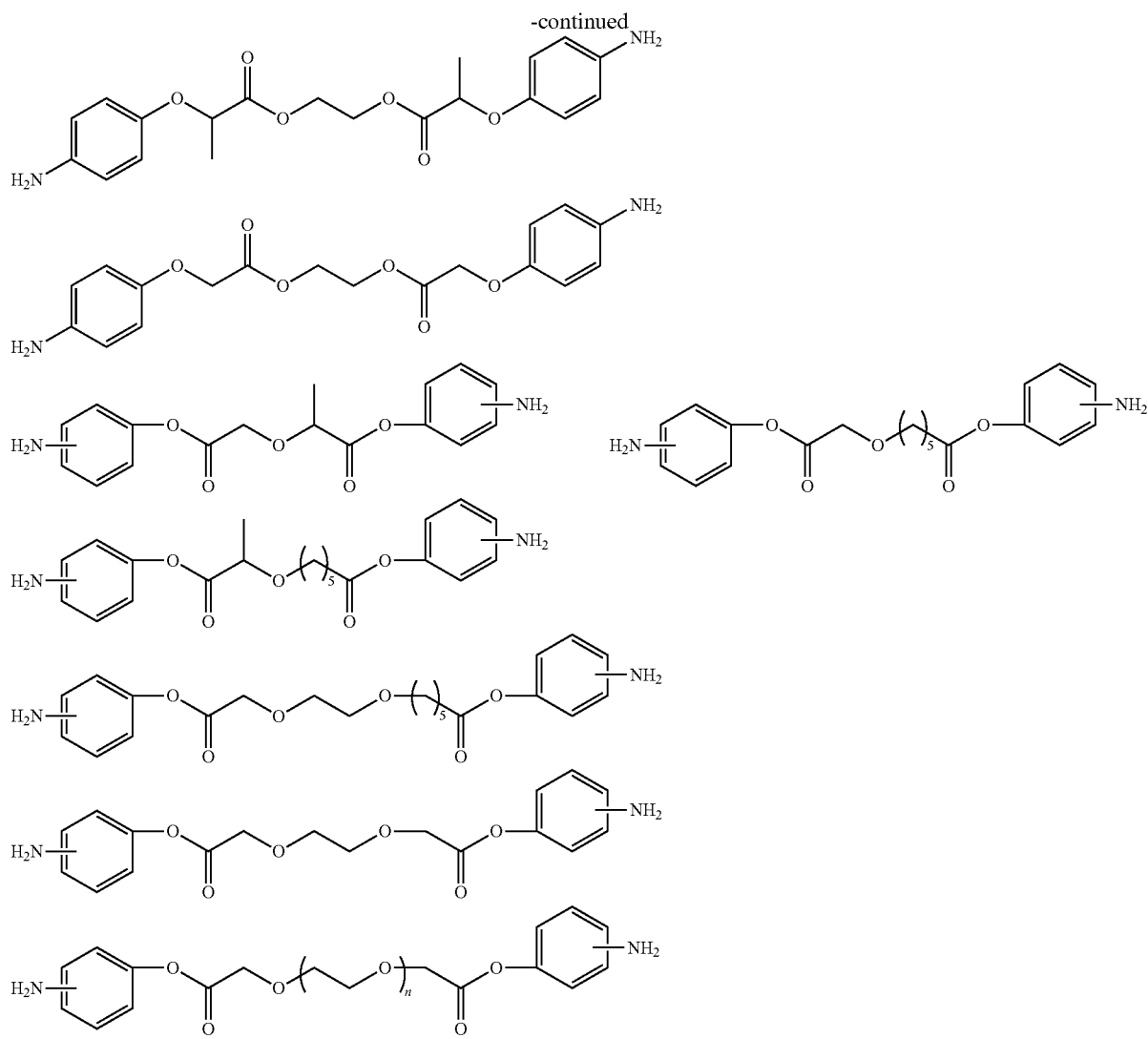
wherein n is selected from 10, 11, and 12.
24. The surgical article of claim 1, wherein the article is a polyamideurethane formed by polymerizing a biocompatible and bioabsorbable polyisocyanate of Formula I with an amide-diol selected from:
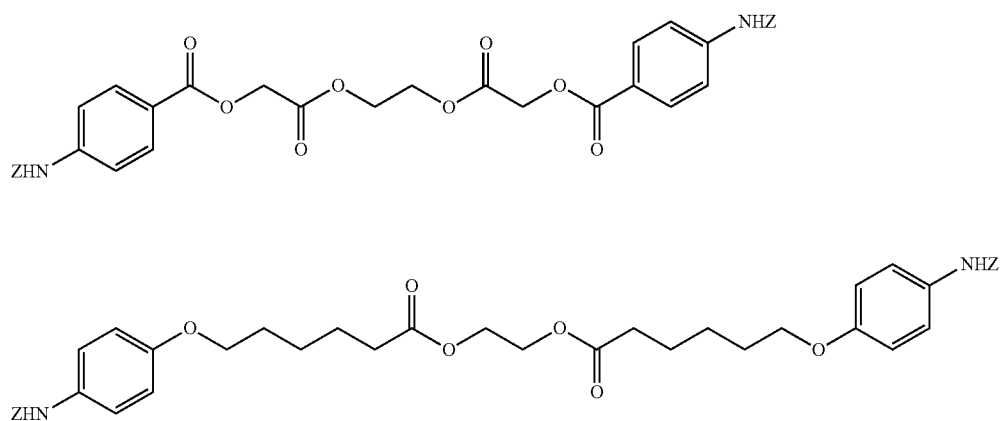

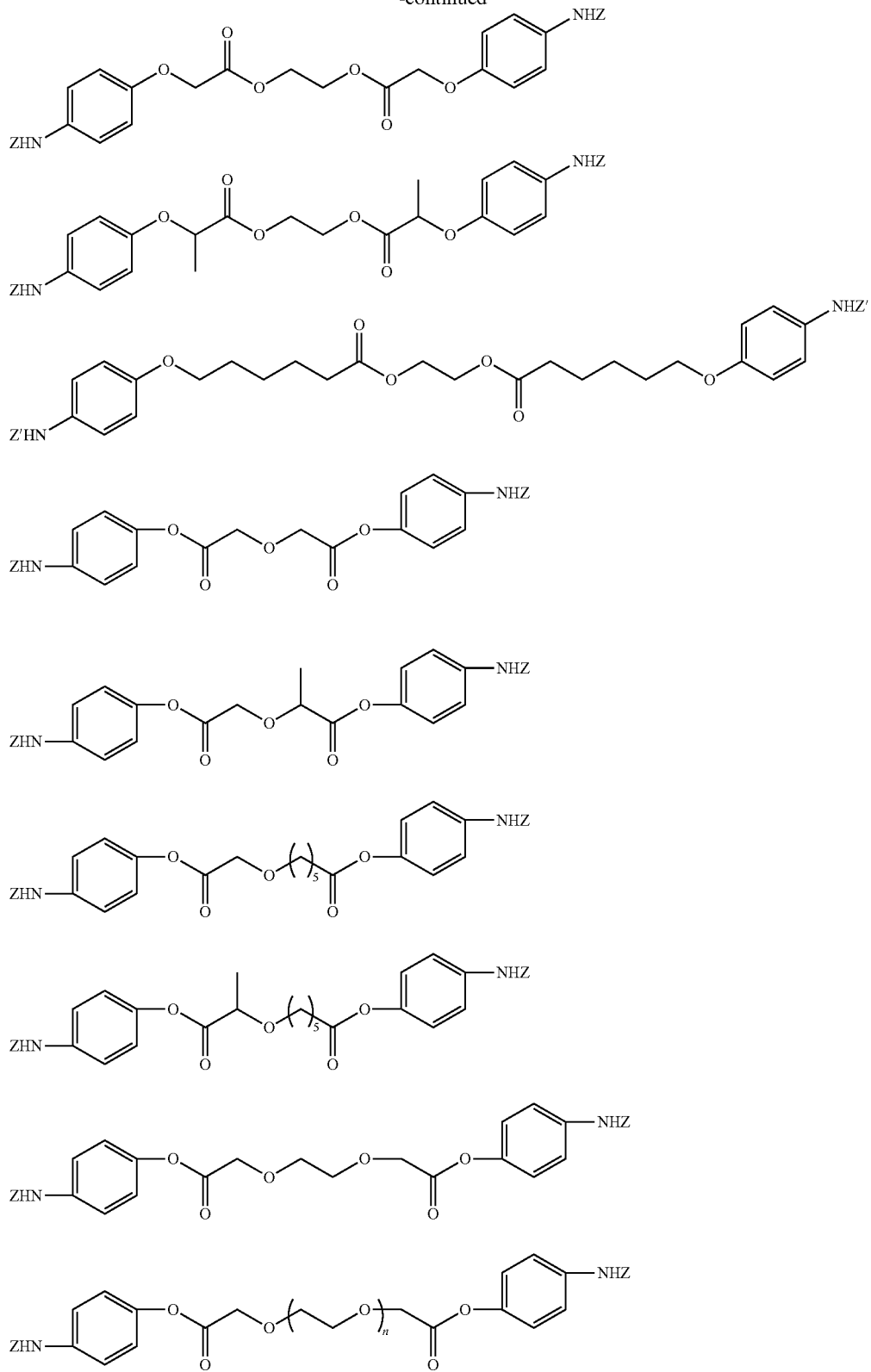
wherein:
Z=C(O)CH$_2$OC(O)CH$_2$OH;
Z'=C(O)CH(CH$_3$)OC(O)CH$_2$OH; and,
n is selected from 10, 11, and 12.

25. The surgical article of claim 1, wherein the article is a polyureaurethane formed by polymerizing a biocompatible and bioabsorbable polyisocyanate of Formula I with a polyol and an amine, wherein:
  the polyol is selected from:
   a) 1,2-ethanediol (ethylene glycol);
   b) 1,2-propanediol (propylene glycol);
   c) 1,3-propanediol;
   d) 1,4-butanediol;
   e) 1,5-pentanediol;
   f) 1,3-cyclopentanediol;
   g) 1,6-hexanediol;
   h) 1,8-octanediol;
   i) a polyethylene glycol with a molecular weight from about 500 to about 10000;
   j) polytetramethylene ether glycol; and,
   k) a polyol with a molecular weight of about 500 to about 10000 derived from a compound selected from glycolide, lactide, trimethylenecarbonate, p-dioxanone, caprolactone, and combinations thereof;
  and the amine is selected from:

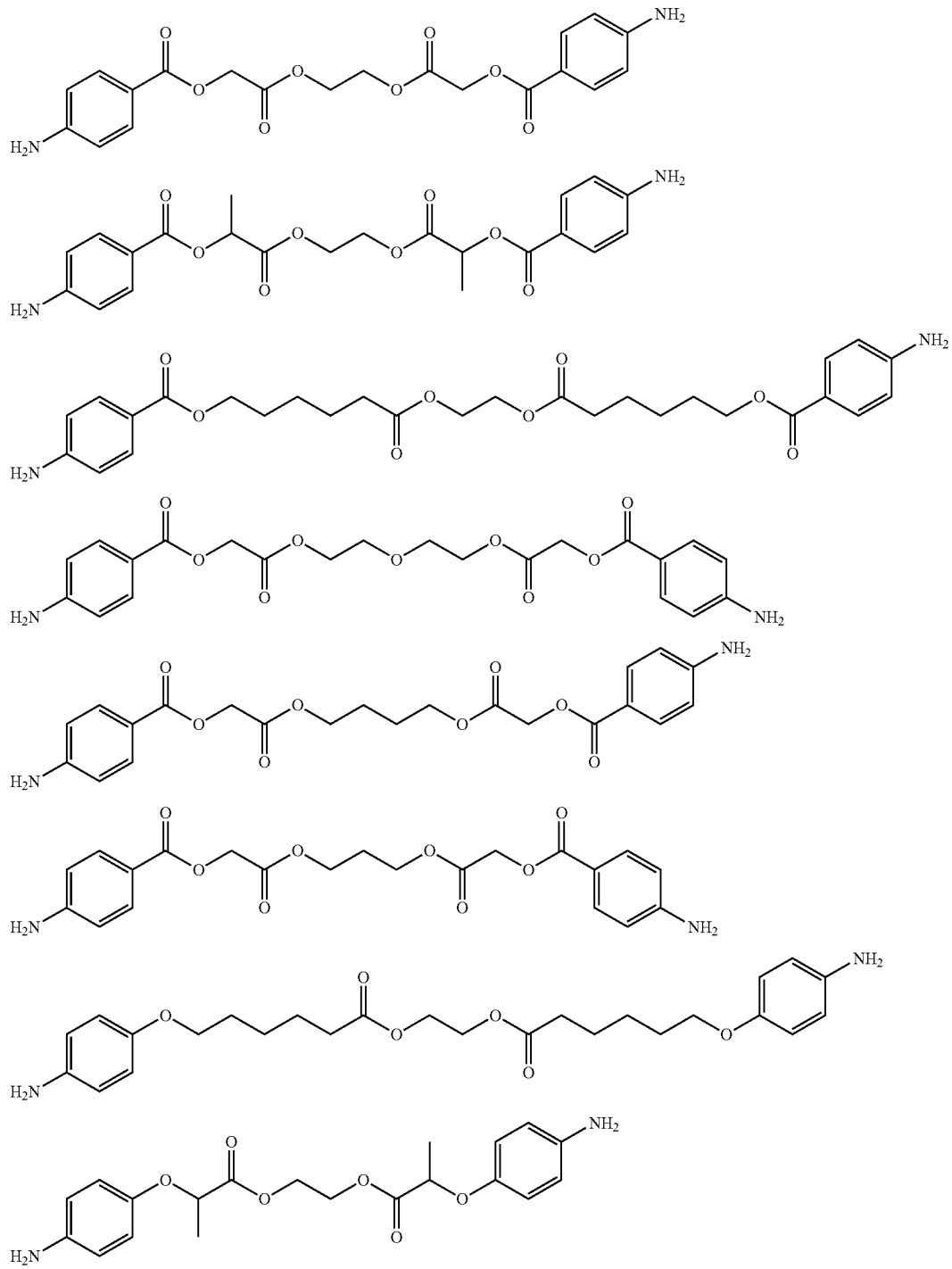

-continued
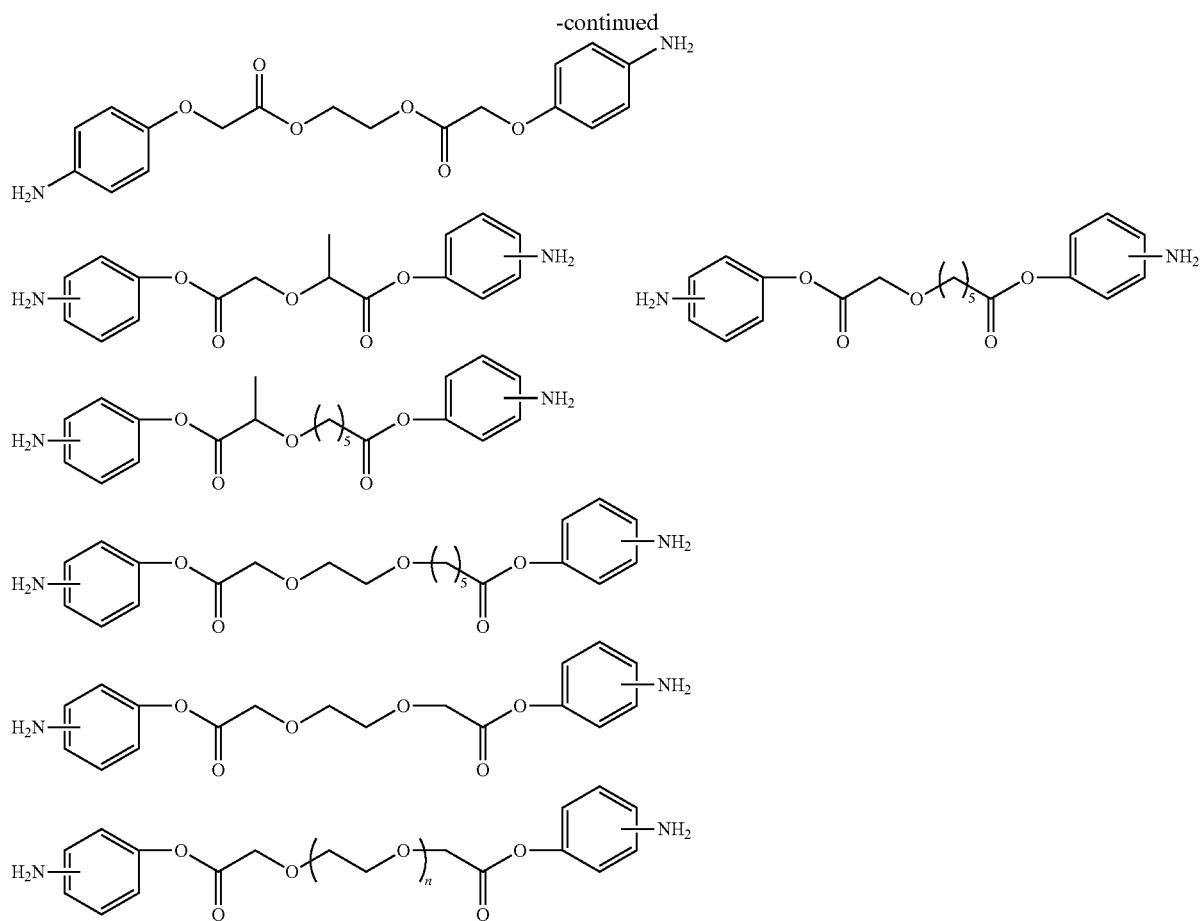
wherein n is selected from 10, 11, and 12.
26. The surgical article of claim 1, wherein the biocompatible and bioabsorbable polyisocyanate of Formula I is a compound of formula Id:
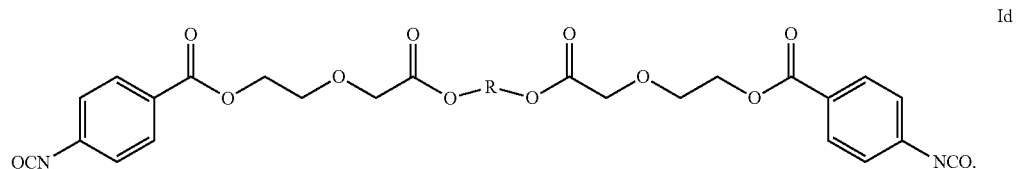
27. The surgical article of claim 26, wherein the biocompatible and bioabsorbable polyisocyanate of Formula I is:
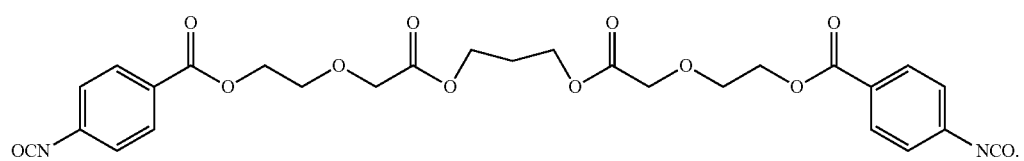

28. The surgical article of claim 14, wherein the biocompatible and bioabsorbable polyisocyanate of Formula I is a compound of Formula Ic:

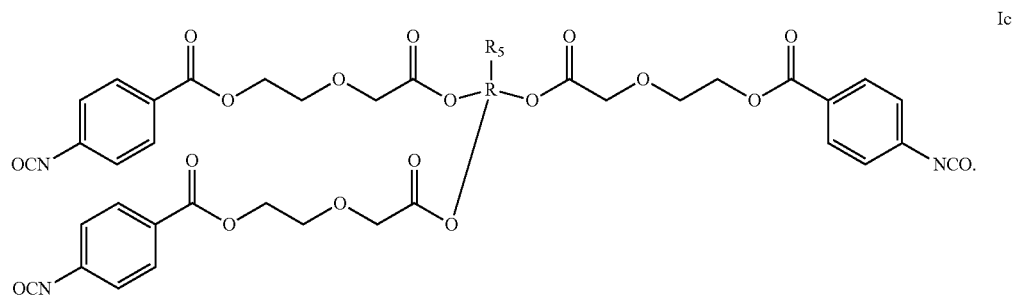

29. The surgical article of claim 28, wherein $R^5=C_{1-3}$ alkyl.

30. The surgical article of claim 28, wherein $R^5$=ethyl.

31. The surgical article of claim 28, wherein $R^5=CH_2-(Y^2)_aOR^6$.

32. The surgical article of claim 14, wherein the biocompatible and bioabsorbable polyisocyanate of Formula I is a compound of Formula Ie:

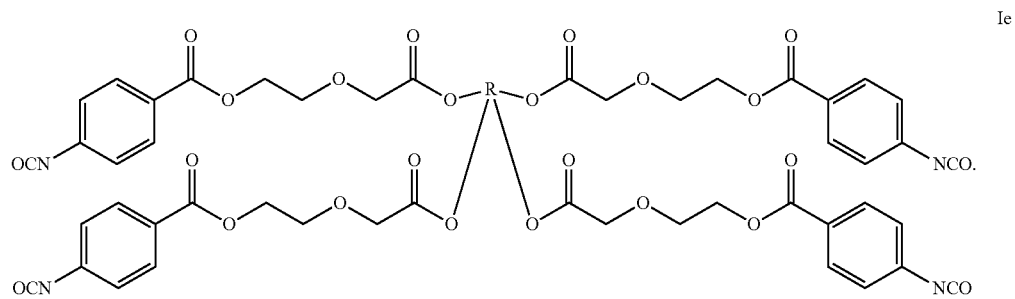

33. The surgical article of claim 14, wherein the article is a polyurethane is formed by polymerizing a biocompatible and bioabsorbable polyisocyanate of Formula Ib with a polyol selected from:

l) 1,2-ethanediol (ethylene glycol);

m) 1,2-propanediol (propylene glycol);

n) 1,3-propanediol;

o) 1,4-butanediol;

p) 1,5-pentanediol;

q) 1,3-cyclopentanediol;

r) 1,6-hexanediol;

s) 1,8-octanediol;

t) a polyethylene glycol with a molecular weight from about 500 to about 10000;

u) polytetramethylene ether glycol; and, v) a polyol with a molecular weight of about 500 to about 10000 derived from a compound selected from glycolide, lactide, trimethylenecarbonate, p-dioxanone, caprolactone, and combinations thereof.

34. The surgical article of claim 14, wherein the article is a polyurea formed by polymerizing a biocompatible and bioabsorbable polyisocyanate of Formula Ib with an amine selected from:

73 74
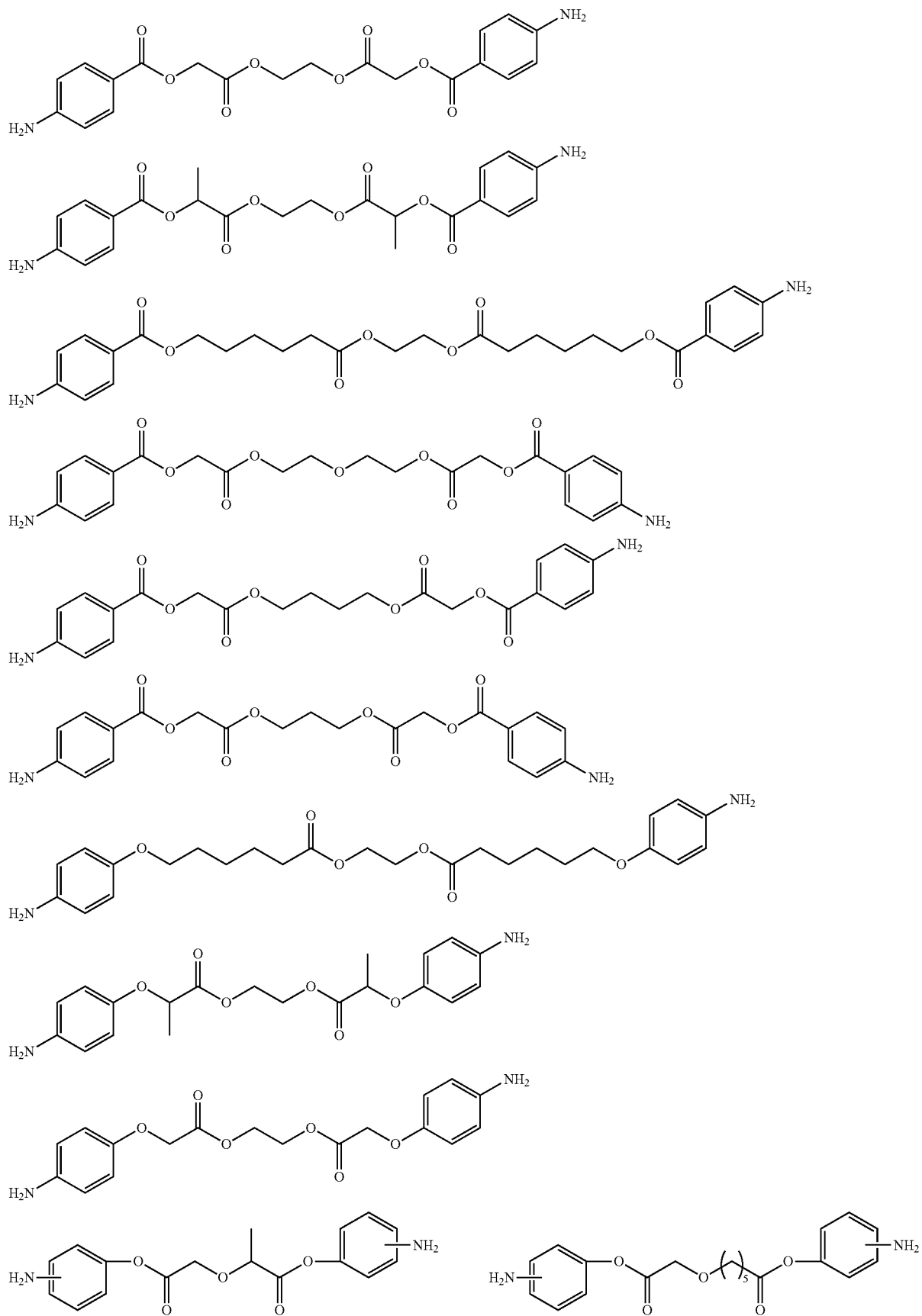

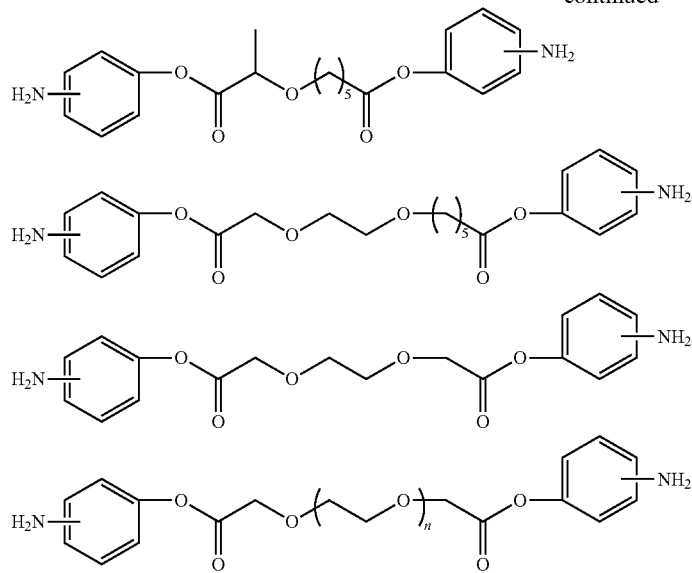
wherein n is selected from 10, 11, and 12.
35. The surgical article of claim 14, wherein the article is a polyamideurethane formed by polymerizing a biocompatible and bioabsorbable polyisocyanate of Formula Ib with an amide-diol selected from:
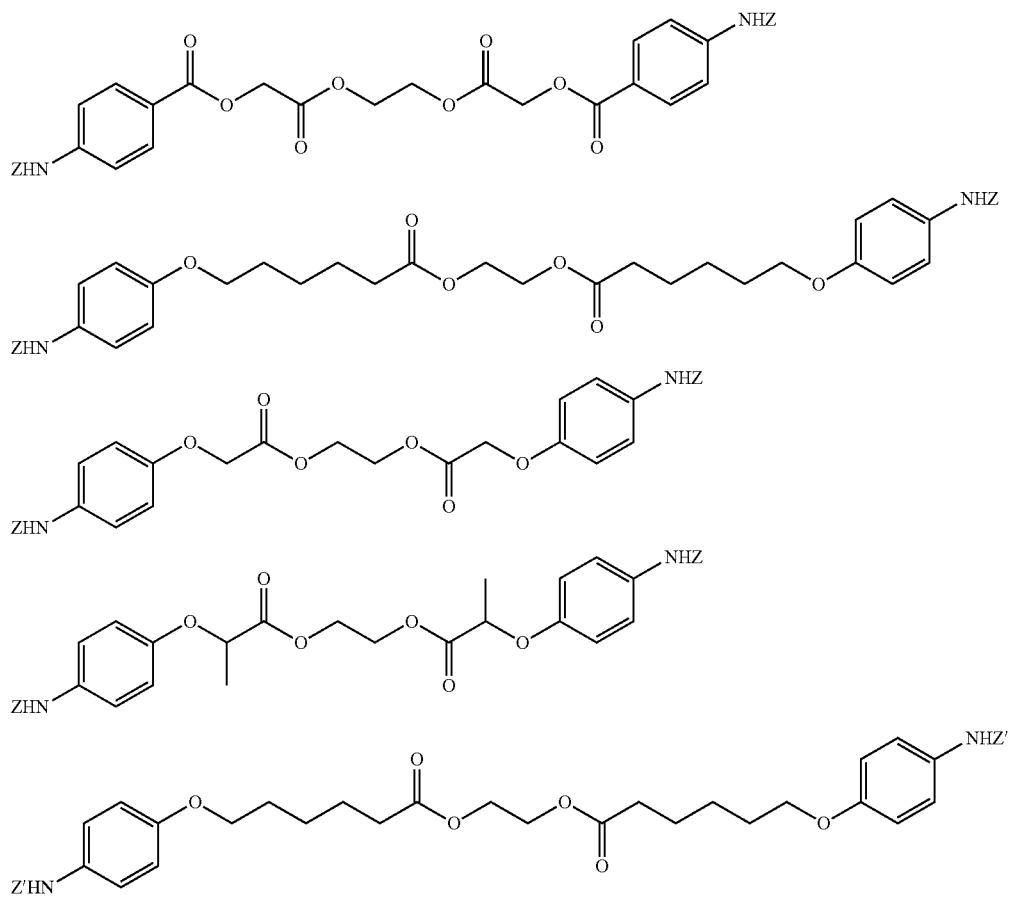

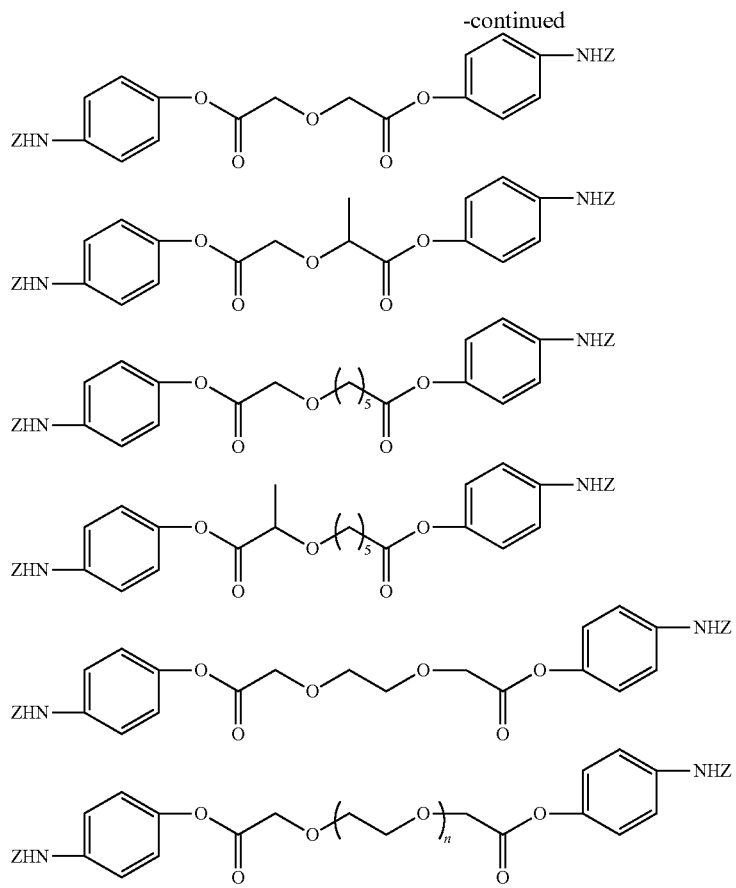

wherein:
Z=C(O)CH$_2$OC(O)CH$_2$OH;
Z'=C(O)CH(CH$_3$)OC(O)CH$_2$OH; and,
n is selected from 10, 11, and 12.

36. The surgical article of claim 14, wherein the article is a polyureaurethane formed by polymerizing a biocompatible and bioabsorbable polyisocyanate of Formula Ib with a polyol and an amine, wherein:
the polyol is selected from:
l) 1,2-ethanediol (ethylene glycol);
m) 1,2-propanediol (propylene glycol);
n) 1,3-propanediol;
o) 1,4-butanediol;
p) 1,5-pentanediol;
q) 1,3-cyclopentanediol;
r) 1,6-hexanediol;
s) 1,8-octanediol;
t) a polyethylene glycol with a molecular weight from about 500 to about 10000;
u) polytetramethylene ether glycol; and,
v) a polyol with a molecular weight of about 500 to about 10000 derived from a compound selected from glycolide, lactide, trimethylenecarbonate, p-dioxanone, caprolactone, and combinations thereof;
and the amine is selected from:

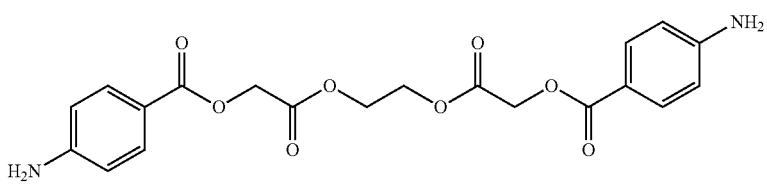

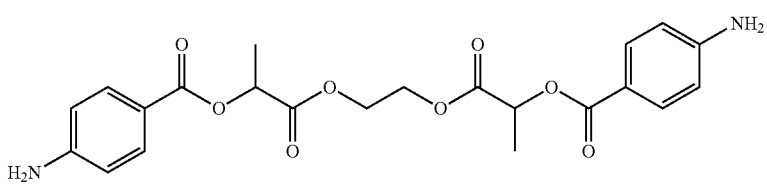

-continued
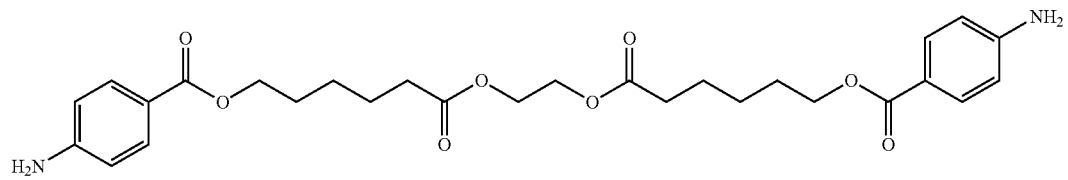
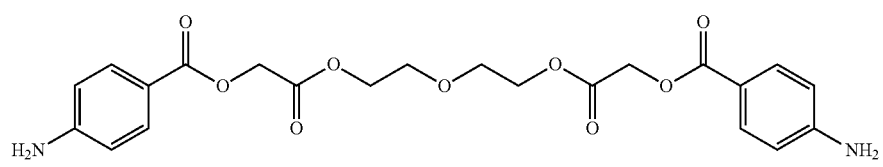
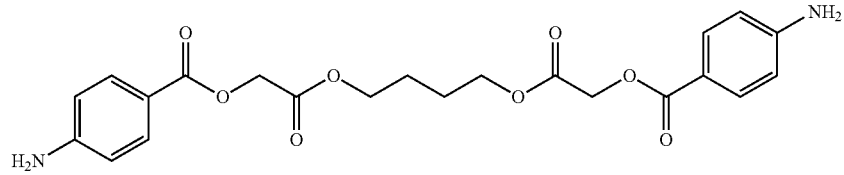
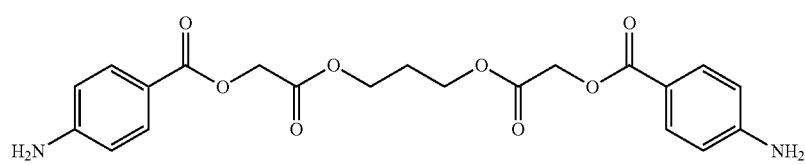
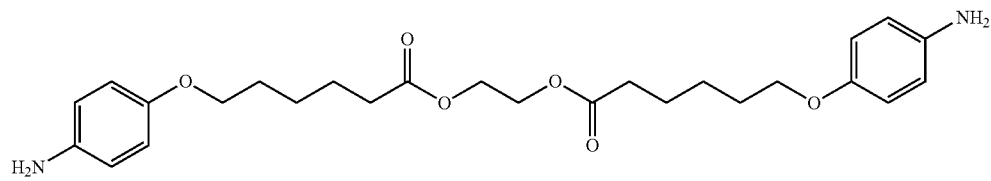
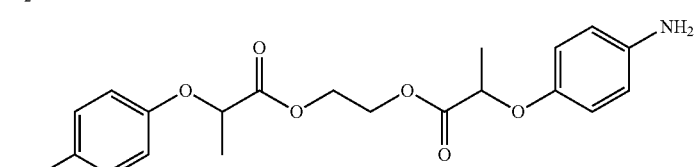
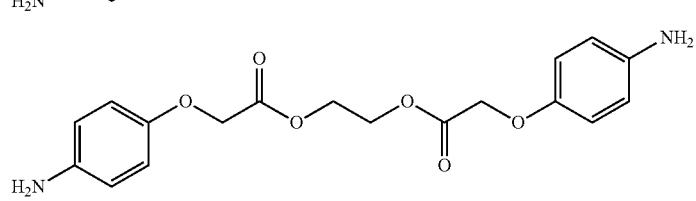
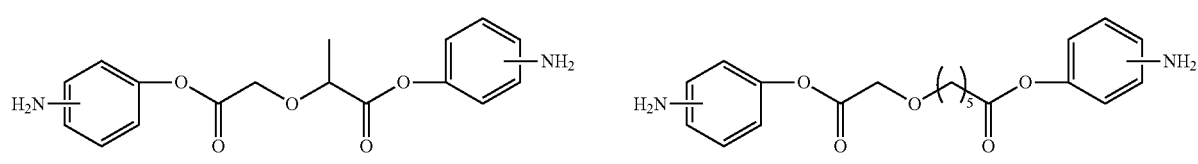
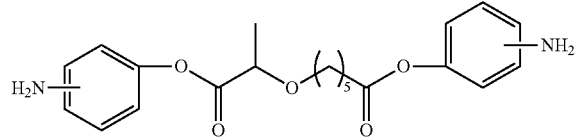
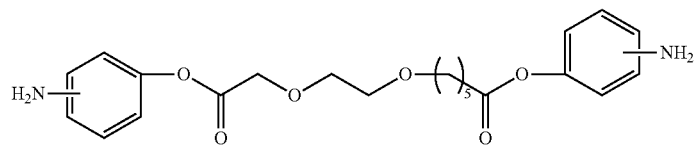

-continued
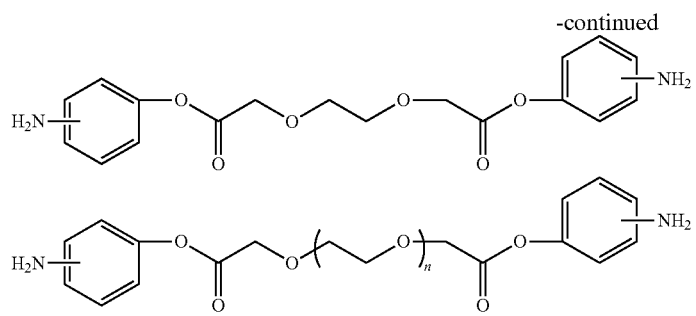
wherein n is selected from 10, 11, and 12.
* * * * *